United States Patent
Kaneko et al.

(10) Patent No.: US 9,726,744 B2
(45) Date of Patent: Aug. 8, 2017

(54) MAGNETIC RESONANCE IMAGING EQUIPMENT, HIGH FREQUENCY MAGNETIC FIELD IRRADIATION METHOD AND PROGRAM

(75) Inventors: Yukio Kaneko, Tokyo (JP); Yoshihisa Soutome, Tokyo (JP); Yoshitaka Bito, Tokyo (JP); Hiroyuki Takeuchi, Tokyo (JP); Tetsuhiko Takahashi, Tokyo (JP); Hideta Habara, Tokyo (JP); Yosuke Otake, Tokyo (JP)

(73) Assignee: HITACHI, LTD., Tokyo (JP)

( * ) Notice: Subject to any disclaimer, the term of this patent is extended or adjusted under 35 U.S.C. 154(b) by 621 days.

(21) Appl. No.: 14/241,515

(22) PCT Filed: Jul. 27, 2012

(86) PCT No.: PCT/JP2012/069239
§ 371 (c)(1),
(2), (4) Date: Mar. 27, 2014

(87) PCT Pub. No.: WO2013/046900
PCT Pub. Date: Apr. 4, 2013

(65) Prior Publication Data
US 2014/0292334 A1    Oct. 2, 2014

(30) Foreign Application Priority Data
Sep. 29, 2011 (JP) .................... 2011-214865

(51) Int. Cl.
*G01R 33/565* (2006.01)
*G01R 33/24* (2006.01)
(Continued)

(52) U.S. Cl.
CPC .......... *G01R 33/5659* (2013.01); *A61B 5/055* (2013.01); *G01R 33/246* (2013.01); *G01R 33/4835* (2013.01); *G01R 33/5612* (2013.01)

(58) Field of Classification Search
CPC .............. G01R 33/5659; G01R 33/246; G01R 33/4835; G01R 33/5612; A61B 5/055
See application file for complete search history.

(56) References Cited

U.S. PATENT DOCUMENTS

| | | |
|---|---|---|
| 7,078,901 B2 | 7/2006 | Feiweier et al. |
| 2006/0049829 A1 | 3/2006 | Takizawa et al. |

(Continued)

FOREIGN PATENT DOCUMENTS

| | | |
|---|---|---|
| JP | 2007-283104 | 11/2007 |
| JP | 2010-29640 | 2/2010 |
| JP | 2010-508054 | 3/2010 |
| WO | WO 2010/032172 A1 | 3/2010 |

OTHER PUBLICATIONS

J. Nistler et al., Homogeneity Improvement Using a 2 Port Birdcage Coil, Proc. Intl. Soc. Mag. Reson. Med. 15 (2007).

(Continued)

*Primary Examiner* — Rodney Bonnette
(74) *Attorney, Agent, or Firm* — Baker Botts L.L.P.

(57) ABSTRACT

Systems and methods for magnetic resonance imaging, including adjusting spatial distribution of a rotating magnetic field. By minimizing imaging time, the $B_1$ nonuniformity reducing effect of RF shimming is maximized for an imaging section of an arbitrary axis direction and an arbitrary position. $B_1$ distributions are measured for only several sections of one predetermined direction, and a radio frequency magnetic field condition that maximizes the $B_1$ non-uniformity reducing effect for an imaging section of an arbitrary direction and an arbitrary position is calculated from the $B_1$ distribution data.

16 Claims, 19 Drawing Sheets

(51) Int. Cl.
*A61B 5/055* (2006.01)
*G01R 33/483* (2006.01)
*G01R 33/561* (2006.01)

(56) References Cited

U.S. PATENT DOCUMENTS

| | | |
|---|---|---|
| 2006/0106299 A1 | 5/2006 | Uchizono et al. |
| 2007/0255128 A1 | 11/2007 | Nistler |
| 2008/0265889 A1* | 10/2008 | Zhai .................. G01R 33/3415 324/318 |
| 2009/0322330 A1 | 12/2009 | Adachi et al. |
| 2010/0016708 A1 | 1/2010 | Katscher et al. |
| 2011/0156704 A1* | 6/2011 | Boernert ............ G01R 33/3415 324/309 |
| 2013/0082708 A1* | 4/2013 | Yokosawa .............. A61B 5/055 324/309 |
| 2015/0241539 A1* | 8/2015 | Kaneko .................. A61B 5/055 324/307 |

OTHER PUBLICATIONS

G. Ferrand et al., Accelerating Parallel Transmit Array B1 Mapping in High Field MRI with Slice Undersampling and Interpolation by Kriging, IEEE Transactions on Medical Imaging, vol. 33, No. 8, Aug. 2014, pp. 1726-1734.

Extended European Search Report, dated May 13, 2015, which issued during the prosecution of European Patent Application No. 12836712.5, which corresponds to the present application.

* cited by examiner

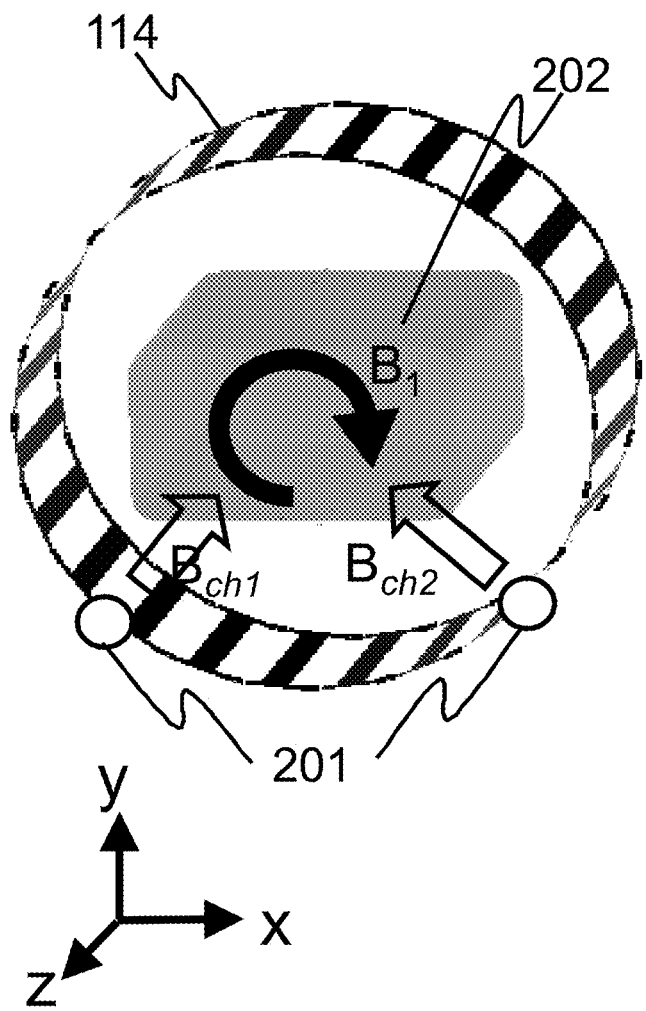

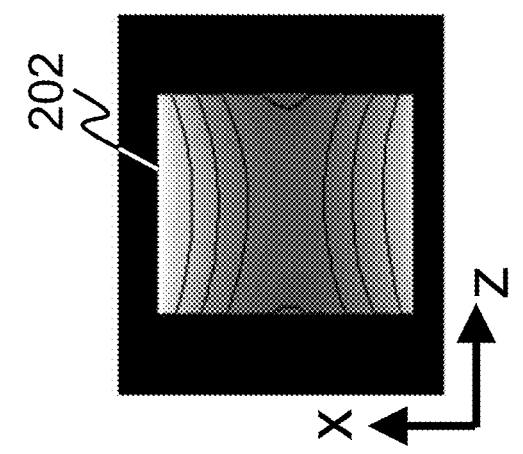 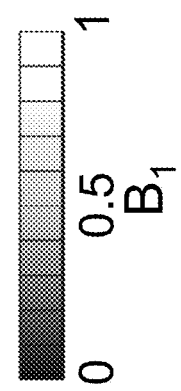
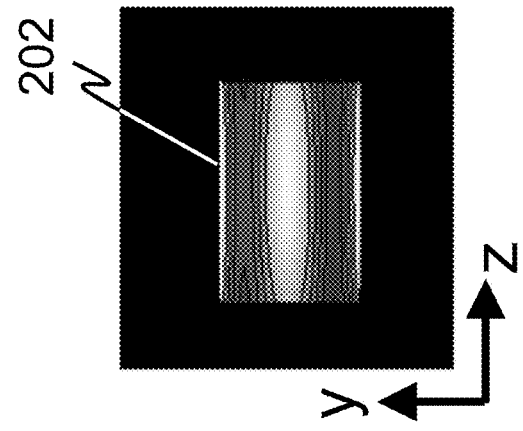 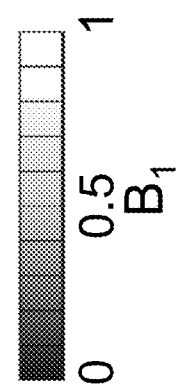
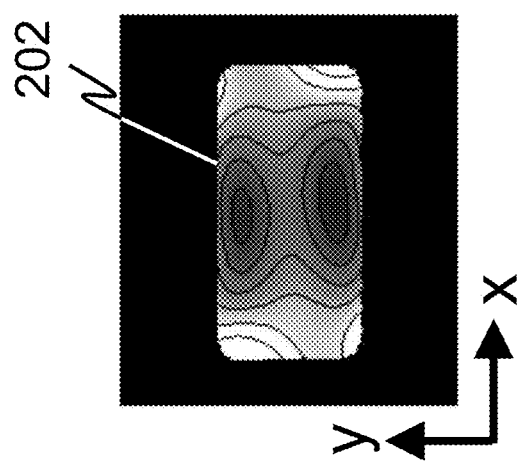 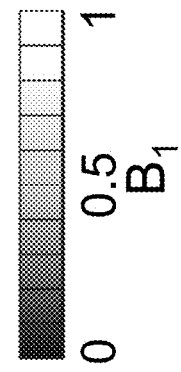
Fig. 3A  Fig. 3B  Fig. 3C

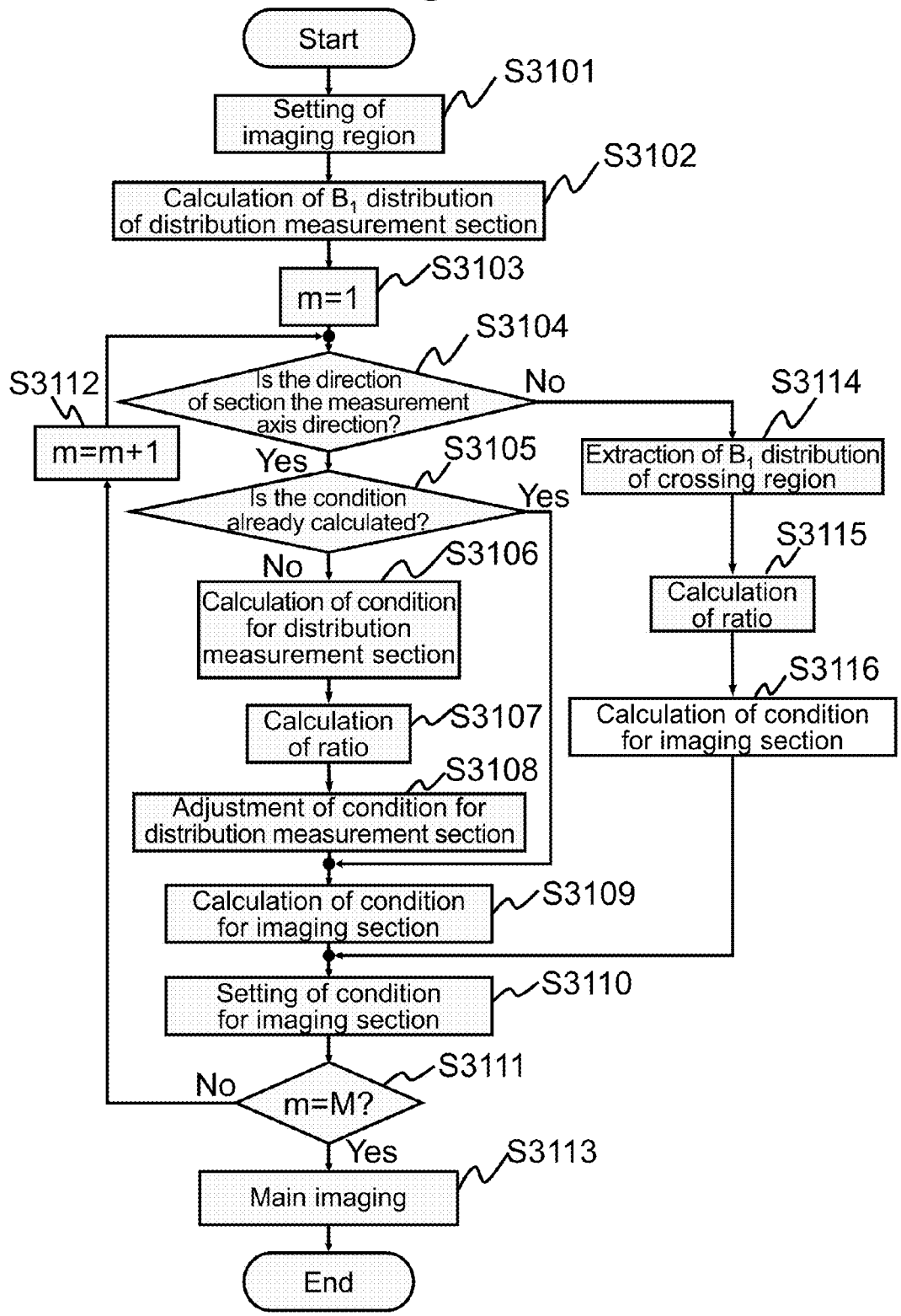

MAGNETIC RESONANCE IMAGING EQUIPMENT, HIGH FREQUENCY MAGNETIC FIELD IRRADIATION METHOD AND PROGRAM

TECHNICAL FIELD

The present invention relates to a magnetic resonance imaging (MRI) apparatus (henceforth referred to as MRI apparatus). In particular, the present invention relates to a technique for adjusting spatial distribution of rotating magnetic field, which induces the magnetic resonance phenomenon.

BACKGROUND ART

MRI apparatuses are diagnostic imaging apparatuses for medical use, which induce magnetic resonance of atomic nuclei in an arbitrary cross section of a test subject to generate magnetic resonance signals, and obtain a tomographic image from the signals. The apparatuses transmit a radio frequency wave (henceforth also referred to as high frequency wave or RF), a kind of electromagnetic waves, to the test subject to excite spins of the atomic nuclei in the test subject, then receive the magnetic resonance signals generated by the nuclear spins, and reconstruct an image of the test subject. The transmission is performed with an RF transmission coil, and the reception is performed with an RF reception coil.

In recent years, in order to improve SNR (signal to noise ratio) of the image, it tends to use a static magnetic field of higher intensity, and use of high magnetic field MRI apparatuses using a static magnetic field strength of 3 T (tesla) or higher (3T MRI apparatuses) begins to spread. However, as the static magnetic field intensity becomes higher, obtained images more easily suffer from non-uniformity of the images. This is because the frequency of RF used in order to induce the magnetic resonance phenomenon becomes higher with use of the higher magnetic field intensity. For example, the 3T MRI apparatuses use RF having a frequency of 128 MHz, and this wavelength of RF in living bodies is about 30 cm, which is in substantially the same scale as that of a section of the abdominal part, and gives phase change of RF in the living bodies. Therefore, irradiated RF distribution and spatial distribution of rotating magnetic field (henceforth referred to as $B_1$) generated by RF to induce the magnetic resonance phenomenon become uneven to cause the image non-uniformity. Under such a current situation, there is desired a technique for reducing the non-uniformity of the distribution of the rotating magnetic field $B_1$ at the time of RF irradiation performed in high magnetic field MRI apparatuses, in order to improve image quality.

As methods for reducing the non-uniformity of $B_1$ distribution, several techniques of devising the RF irradiation method have been proposed. Among them, a technique called "RF shimming" has appeared and attracts attention in recent years. This is a method of using an RF transmission coil having two or more channels and controlling phases and amplitudes of RF to be applied to the channels to reduce the $B_1$ non-uniformity in imaging regions.

In the RF shimming, in general, the $B_1$ distribution of each channel is measured before the image acquisition, and amplitude and phase of RF for reducing the $B_1$ non-uniformity are calculated by using that $B_1$ distribution (refer to, for example, Patent document 1 and Non-patent document 1). There is also a technique of performing imaging by setting a region of interest (ROI) and using at least one of amplitude and phase of RF as an imaging condition so as to reduce the $B_1$ non-uniformity in ROI (refer to, for example, Patent document 2). In the technique described in Patent document 2, when a plurality of ROIs are set, obtained is at least one of such amplitude and phase of RF that variation of data among the plurality of ROIs is reduced. A problem that the influence of the $B_1$ non-uniformity differs depending on the characteristics of individual subjects is thereby solved.

PRIOR ART REFERENCES

Patent Documents

Patent document 1: U.S. Pat. No. 7,078,901
Patent document 2: Japanese Patent Unexamined Publication (KOKAI) No. 2010-29640

Non-Patent Document

Non-patent document 1: Nistler J., et al., "Homogeneity Improvement Using A 2 Port Birdcage Coil", Proceedings of International Society of Magnetic Resonance in Medicine 2007, p. 1063

DISCLOSURE OF THE INVENTION

Object to be Achieved by the Invention

According to Patent document 1 and Non-patent document 1, the $B_1$ distribution of an imaging section is measured beforehand, and amplitude and phase of the RF pulse for reducing the $B_1$ non-uniformity are calculated on the basis of the measured $B_1$ distribution. However, in actual image acquisition, a plurality of images are obtained for sections at various positions along directions perpendicular to various axes (henceforth referred to as axis directions). The axis directions generally has the three kinds of directions including axial (henceforth referred to as AX), sagittal (henceforth referred to as SAG), and coronal (henceforth referred to as COR) directions, as well as axis directions oblique to the foregoing directions by certain angles (oblique directions). Further, the number of the sections is several to several tens for one direction, in many cases.

Therefore, when the techniques of Patent document 1 and Non-patent document 1 are used, in order to maximize the $B_1$ non-uniformity reducing effect for all the imaging sections, it is necessary to measure $B_1$ distributions for all the imaging sections, and calculate amplitude and phase of RF optimal for each imaging section, and therefore enormous time is required. Therefore, the total imaging time is extended. On the other hand, if $B_1$ distribution is measured only for a predetermined imaging section, and calculated values of amplitude and phase of one RF are applied to all the other sections, the $B_1$ non-uniformity reducing effect may not fully be obtained for the other sections.

Also with the technique described in Patent document 2, much time is required for measuring $B_1$ distributions for all the imaging sections, and the total imaging time is extended.

The present invention was accomplished in light of the aforementioned circumstances, and provides a technique for maximizing the $B_1$ non-uniformity reducing effect of the RF shimming for an imaging section along an arbitrary axial direction and at an arbitrary position, with minimizing extension of the imaging time.

Means for Achieving the Object

According to the present invention, amplitude and phase of RF for maximizing the $B_1$ non-uniformity reducing effect for an arbitrary imaging section are calculated by using $B_1$ distributions of a predetermined number of sections along a predetermined axis direction, as well as amplitude and phase of RF that maximize the $B_1$ non-uniformity reducing effect.

Representative aspects of the present invention are, for example, as follows. That is, the present invention provides a magnetic resonance imaging apparatus comprising a static magnetic field formation part for forming a static magnetic field, a gradient magnetic field application part for applying a gradient magnetic field, a radio frequency magnetic field transmission part having a plurality of channels for transmitting different radio frequency magnetic fields to a subject, a signal reception part for receiving magnetic resonance signals generated from the subject, a distribution calculation part for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and a condition calculation part for calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution.

The present invention also provides a method for determining an imaging condition for reducing non-uniformity of a radio frequency magnetic field in a magnetic resonance imaging apparatus comprising a radio frequency magnetic field transmission part having a plurality of channels for transmitting different radio frequency magnetic fields to a subject, and a signal reception part for receiving magnetic resonance signals generated from the subject, which comprises a distribution calculation step of calculating a first radio frequency magnetic field distribution as a radio frequency magnetic field distribution of a first distribution measurement section perpendicular to a first axis from the magnetic resonance signals detected by the signal reception part after the radio frequency magnetic fields are transmitted from the radio frequency magnetic field transmission part to the subject, and a condition calculation step of calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution.

Effect of the Invention

According to the present invention, the $B_1$ non-uniformity reducing effect of the RF shimming is maximized for all imaging sections of arbitrary axis directions and arbitrary positions, with minimizing extension of the imaging time.

BRIEF DESCRIPTION OF THE DRAWINGS

FIG. 2 is an explanatory drawing for explaining a transmission coil of the first embodiment, phantom, and rotating magnetic field.

FIG. 3A is an explanatory drawing for explaining simulation result showing the rotating magnetic field $B_1$ distribution in an AX section of a phantom.

FIG. 3B is an explanatory drawing for explaining simulation result showing the rotating magnetic field $B_1$ distribution in an SAG section of the phantom.

FIG. 3C is an explanatory drawing for explaining simulation result showing the rotating magnetic field $B_1$ distribution in a COR section of the phantom.

FIG. 19 is a flowchart of imaging processing according to the third embodiment.

MODES FOR CARRYING OUT THE INVENTION

Figure 1:
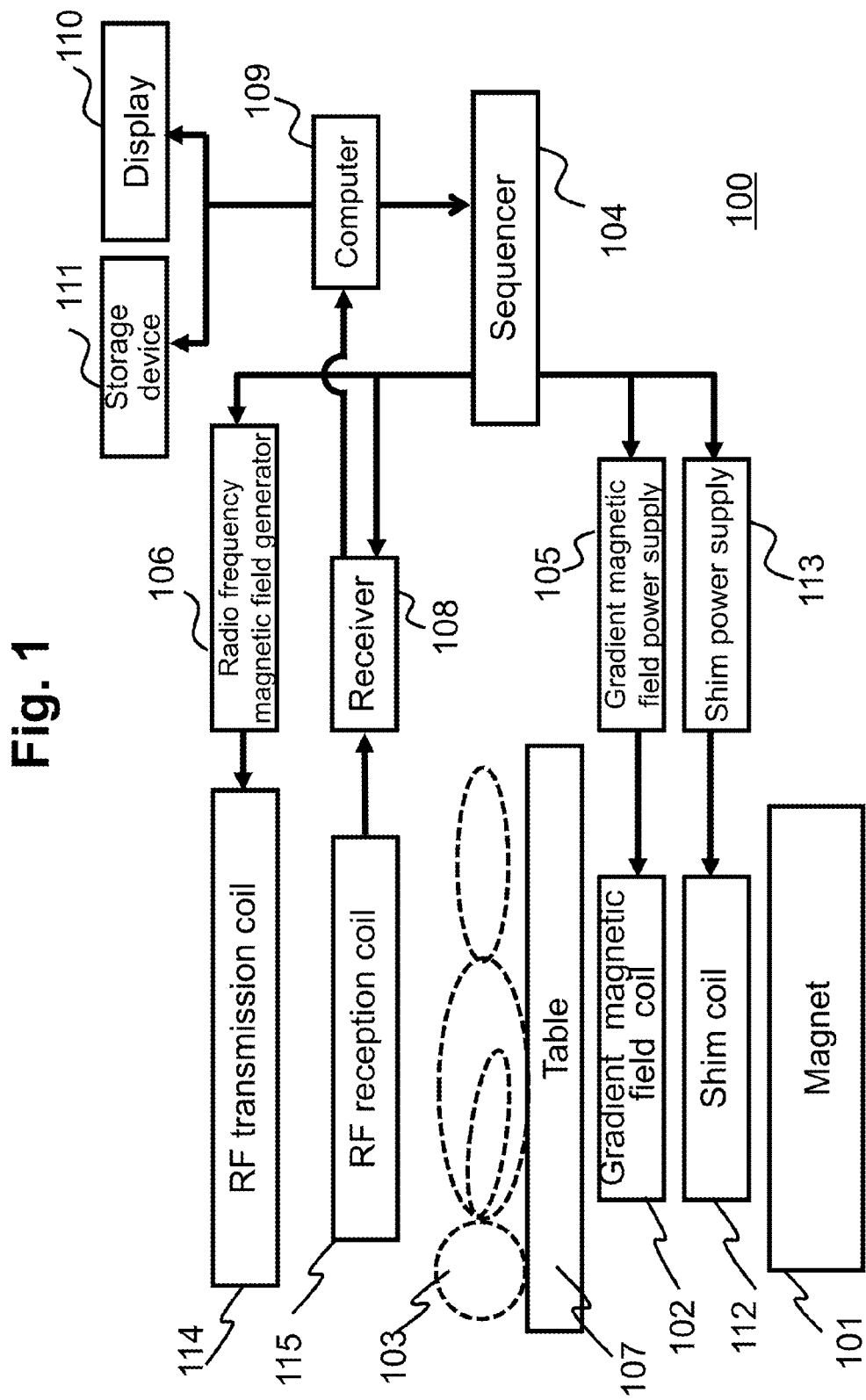
FIG. 1 is a configurational diagram showing outline of an MRI apparatus according to the first embodiment.

First, the outline of the present invention will be explained. According to the present invention, amplitude and phase of RF that maximize the $B_1$ non-uniformity reducing effect for an arbitrary imaging section are calculated from $B_1$ distributions of a predetermined number of sections of a predetermined axis direction, as described above.

Specifically, $B_1$ distributions (henceforth also referred to as radio frequency magnetic field distribution) of a plurality of different sections perpendicular to one axis defined beforehand are measured. Then, by using these $B_1$ distributions, at least one of amplitude and phase of a radio frequency magnetic field (RF) used as an imaging condition for imaging of an arbitrary imaging section is calculated. The amplitude and phase of RF to be calculated are those maximizing the $B_1$ distribution non-uniformity reducing effect for the imaging section.

In the present specification, the section for which $B_1$ distribution is measured is henceforth referred to as distribution measurement section, and an axis perpendicular to the distribution measurement section is henceforth referred to as distribution measurement axis. Further, at least one of amplitude and phase of RF to be calculated as an imaging condition is referred to as radio frequency magnetic field condition. Further, a radio frequency magnetic field condition that maximizes the $B_1$ distribution non-uniformity reducing effect is referred to as optimal radio frequency magnetic field condition. Furthermore, a section perpendicular to a predetermined axis is referred to as a section of that axis direction.

The optimal radio frequency magnetic field condition for an imaging section at an arbitrary position along the $B_1$ distribution measurement axis direction is calculated by interpolation with optimal radio frequency magnetic field conditions for distribution measurement sections calculated from the $B_1$ distributions of the plurality of distribution measurement sections.

Further, the optimal radio frequency magnetic field condition for an imaging section at an arbitrary position along an axis direction different from the $B_1$ distribution measurement axis is calculated so as to minimize dispersion of $B_1$ values of regions containing lines of intersection of the distribution measurement sections and the imaging section (henceforth referred to as crossing regions) extracted from the $B_1$ distributions of the distribution measurement sections.

In addition, the number of distribution measurement section may be one. In this case, as the optimal radio frequency magnetic field condition for an imaging section at an arbitrary position of the $B_1$ distribution measurement axis direction, a radio frequency magnetic field condition obtained from the $B_1$ distribution of this one distribution measurement section is used as it is. Further, as for the optimal radio frequency magnetic field condition for an imaging section at an arbitrary position of an axis direction different from the $B_1$ distribution measurement axis, $B_1$ values of the crossing regions are extracted from this $B_1$ distribution, and the optimal radio frequency magnetic field condition is calculated on the basis of these values.

First Embodiment

The first embodiment of the present invention will be explained below. First, entire configuration of an MRI apparatus according to the first embodiment will be explained. FIG. 1 is a block diagram of an MRI apparatus 100 according to this embodiment. As shown in this drawing, the MRI apparatus 100 according to this embodiment is provided with a magnet 101 for generating a static magnetic field, a gradient magnetic field coil 102 for generating a gradient magnetic field, a shim coil 112 for adjusting uniformity of static magnetic field, a sequencer 104, an RF transmission coil (transmission coil) 114 for transmitting a radio frequency (RF) magnetic field, an RF reception coil (reception coil) 115 for detecting (receiving) magnetic resonance signals generated from a subject 103, a table 107 for placing the subject 103, a gradient magnetic field power supply 105, a radio frequency magnetic field generator 106, a receiver 108, a shim power supply 113, and a computer 109.

The gradient magnetic field coil 102 and the shim coil 112 are connected to the gradient magnetic field power supply 105 and the shim power supply 113, respectively. The transmission coil 114 and the reception coil 115 are connected to the radio frequency magnetic field generator 106 and the receiver 108, respectively. The sequencer 104 sends commands to the gradient magnetic field power supply 105, the shim power supply 113, and the radio frequency magnetic field generator 106 to make them generate a gradient magnetic field and RF, respectively. RF is irradiated (transmitted) on the subject 103 via the RF transmission coil 114. Magnetic resonance signals generated from the subject 103 irradiated (transmitted) with RF are detected (received) by the reception coil 115, and detection is performed by the receiver 108. The magnetic resonance frequency used as the basis of the detection performed by the receiver 108 is set by the computer 109 through the sequencer 104. The detected signals are sent to the computer 109 via an A/D conversion circuit, and signal processings such as image reconstruction are performed therein. The results are displayed on a display 110 connected to the computer 109. The detected signals and measurement conditions are saved in a storage device 111 connected to the computer 109 as required. The sequencer 104 usually controls the parts so that they operate at timings and intensities programmed beforehand.

The magnet 101, the shim coil 112, and the shim power supply 113 constitute a static magnetic field formation part for forming a static magnetic field space. The gradient coil 102 and the gradient magnetic field power supply 105 constitute a gradient magnetic field application part for applying a gradient magnetic field to the static magnetic field space. Further, the transmission coil 114 and the radio frequency magnetic field generator 106 constitute a radio frequency magnetic field transmission part for irradiating (transmitting) RF to the subject 103. The reception coil 115 and the receiver 108 constitute a signal reception part for detecting (receiving) magnetic resonance signals generated from the subject 103.

Hereafter, RF shimming that reduces $B_1$ non-uniformity will be briefly explained with reference to FIGS. 2 and 3. First, the rotating magnetic field ($B_1$) generated in a phantom 202 that imitates the subject 103 when RF is irradiated from the transmission coil 114 to the phantom 202 will be explained.

FIG. 2 is a schematic drawing of the transmission coil 114 and the phantom 202. FIGS. 3A, 3B and 3C show examples of the $B_1$ distribution in the phantom 202 calculated by electromagnetic field simulation. FIG. 3A shows a simulation result showing rotating magnetic field $B_1$ distribution in an AX section in the phantom, FIG. 3B shows a simulation result showing rotating magnetic field $B_1$ distribution in a SAG section in the phantom, and FIG. 3C shows a simulation result showing rotating magnetic field $B_1$ distribution in a COR section in the phantom. The $B_1$ intensities shown in FIGS. 3A, 3B, and 3C are standardized so that the maximum $B_1$ intensity in the phantom 202 is 1. Further, FIGS. 3B and 3C show $B_1$ distributions within the range of 300 mm along the z-axis direction. In these examples, a coordinate system wherein the direction of the static magnetic field is the z-axis direction is used.

The phantom 202 used in this simulation had a rectangular parallelepiped shape, and sizes of 350 mm, 200 mm, and 600 mm for the x-, y-, and z-axis directions, respectively. This is a size determined by supposing an abdominal part section of a living body. Further, as for the physical property values of the phantom 202, electric conductivity was set to be 0.6 S/m, and dielectric constant was set to be 60. These were determined by supposing the physical property values in a living body.

As the transmission coil 114 for applying a magnetic flux to the phantom 202, a birdcage coil having 24 rungs was used. This birdcage coil (transmission coil 114) had a cylindrical shape having a diameter of 615 mm and the rung length of 500 mm for the z-axis direction, and disposed so that the center axis is parallel to the z-axis. The frequency of RF irradiated (transmitted) from the birdcage coil (transmission coil 114) was set to be 128 MHz supposing a 3T MRI apparatus. Further, the birdcage coil (transmission coil 114) had two of feeding points 201 so as to have a structure enabling two-channel RF transmission. The channels are referred to as channel 1 (ch1) and channel 2 (ch2), respectively. It is sufficient that the number of the feeding points 201 is 2 or larger, and it is not limited to 2. This embodiment will be explained below by exemplifying an example where the transmission coils 114 has two channels.

The electromagnetic field simulation was performed by disposing a cylindrical shield (not shown in the drawing) having a diameter of 655 mm and a length of 900 mm for the z-axis direction outside the birdcage coil (transmission coil 114).

When an electric voltage of a sine wave form is supplied to the feeding points 201, two magnetic fluxes perpendicular to each other are generated. Specifically, if amplitude and phase of voltage supplied to the channel 1 are represented as A1 and Φ1, amplitude and phase of voltage supplied to the channel 2 are represented as A2 and Φ2, the magnetic flux generated by the channel 1 is represented as B_ch1, and the magnetic flux generated by the channel 2 is represented as B_ch2, by applying voltages of A1 sin (ωt+Φ1) and A2 sin (ωt+Φ2) to the feeding points, respectively, magnetic fluxes B_ch1 and B_ch2 are generated.

In the above example, the rotating magnetic field $B_1$ to be generated is represented by the following equation (1).

$$B_1 = (B\_ch1 + i \times B\_ch2)/2 \quad (1)$$

In the conventional MRI apparatuses, the amplitude ratio (A2/A1) of B_ch1 and B_ch2 is set to be 1, and the phase difference (Φ2-Φ1) of the same is set to be Π/2, in order to most efficiently generate this $B_1$. This setting is according to an RF irradiation method called QD (quadrature drive), and is a standard setting.

FIG. 3A shows $B_1$ distribution of an AX section in the case of setting the amplitude ratio and the phase difference as described above (QD irradiation). In this case, it is observed that $B_1$ intensity significantly varies and becomes uneven in the phantom 202. This is the $B_1$ non-uniformity, which is currently regarded as a problem in high magnetic field intensity MRI apparatuses.

In the RF shimming, in order to reduce this $B_1$ non-uniformity, the amplitudes (A1, A2) and phases (Φ1, Φ2) of the voltages supplied to the channel 1 (ch1) and channel 2 (ch2), i.e., amplitudes and phases of RF transmitted from the channels, are adjusted.

Figure 4:
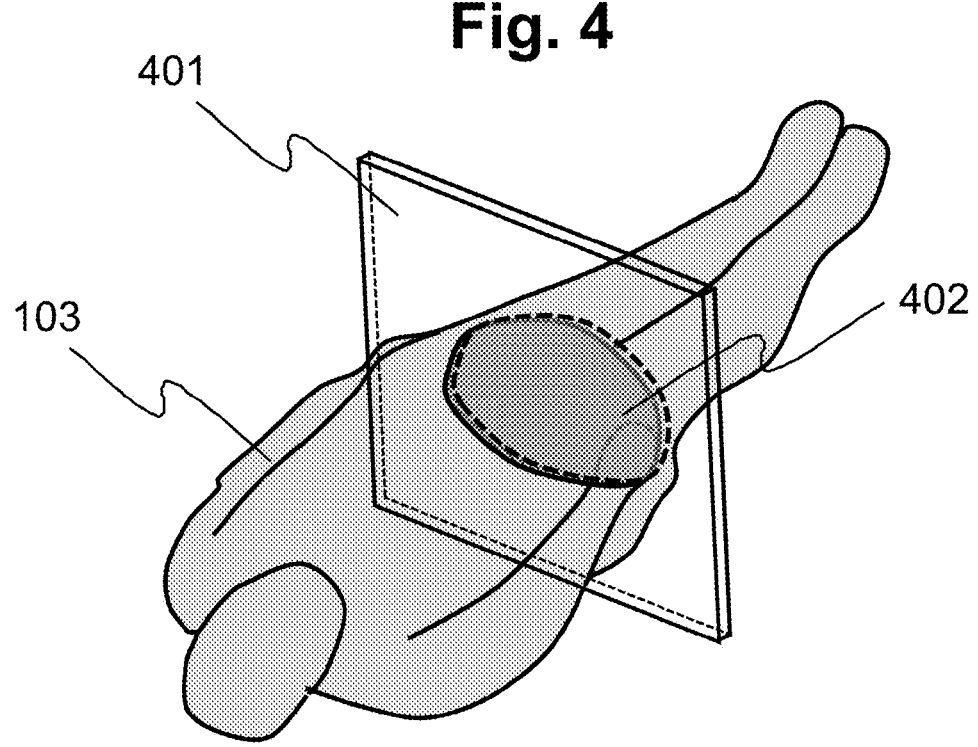
FIG. 4 is an explanatory drawing for explaining an imaging section.

The imaging section will be explained below. FIG. 4 is a drawing for explaining the imaging section in the case where imaging is performed for one predetermined section of a human as the subject 103. This drawing shows an example where an axial (AX) section 401 of a human pelvis region 402 is imaged. In this specification, henceforth human is exemplified as the subject 103, the z-axis direction is defined as the axial (AX) direction, a section perpendicular to the z-axis (section of z-axis direction) is defined as an AX section, the x-axis direction is defined as the sagittal (SAG) direction, a section perpendicular to the x-axis (section of x-axis direction) is defined as a SAG section, the y-axis direction is defined as the coronal (COR) direction, and a section perpendicular to the y-axis (section of y-axis direction) is defined as a COR section.

As shown in this drawing, when one predetermined section is imaged, first, $B_1$ distribution of the pelvis region 402 in the imaging section 401 is measured to obtain the $B_1$ distribution. Then, from the obtained $B_1$ distribution, amplitude and phase of RF optimal for this imaging section 401 are determined, and set as the imaging conditions. The $B_1$ non-uniformity reducing effect can be thereby maximized.

Figure 5A:
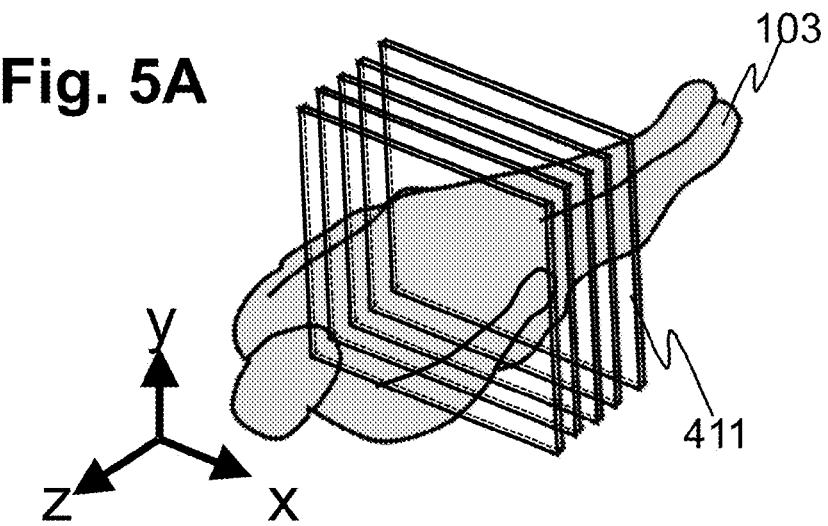
FIG. 5A is an explanatory drawing for explaining position of a section in the case where the imaging section for the image acquisition consists of a plurality of AX sections.
Figure 5B:
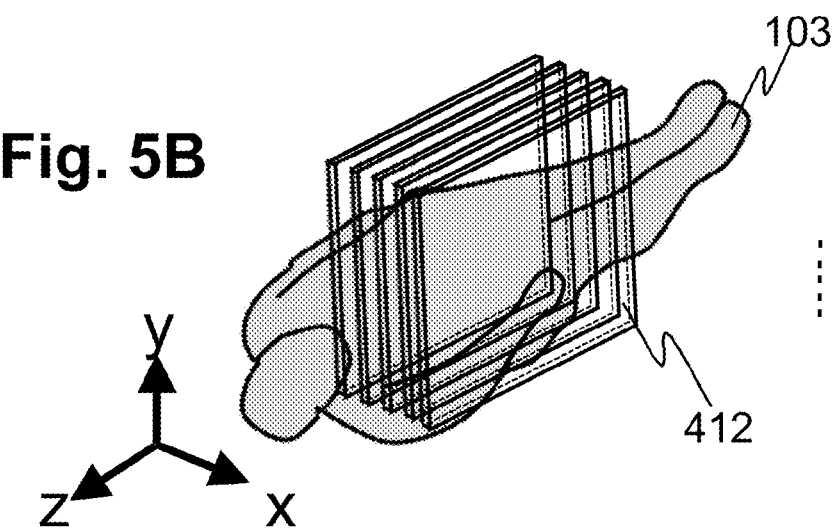
FIG. 5B is an explanatory drawing for explaining position of a section in the case where the imaging section for the image acquisition consists of a plurality of SAG sections.
Figure 5C:
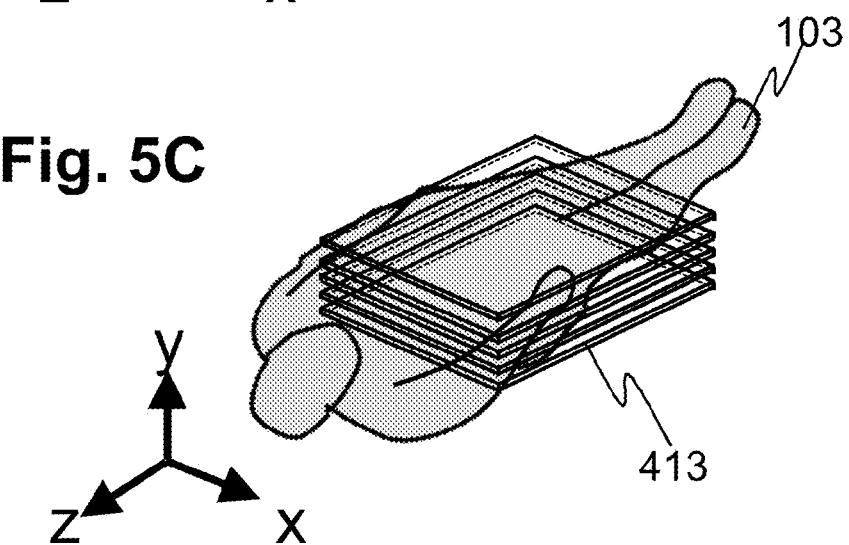
FIG. 5C is an explanatory drawing for explaining position of a section in the case where the imaging section for the image acquisition consists of a plurality of COR sections.

However, the imaging section is not limited to one section at the time of actual imaging (at the time of the image acquisition), and imaging is performed for a plurality of sections of various axis directions. FIG. 5A shows exemplary imaging sections for the case where the imaging is performed for a plurality of AX sections 411, FIG. 5B shows exemplary imaging sections for the case where the imaging is performed for a plurality of SAG sections 412, and FIG. 5C shows exemplary imaging sections for the case where the imaging is performed for a plurality of COR sections 413.

In such imaging of a plurality of imaging sections of various directions as mentioned above, if $B_1$ distributions are measured for all the imaging sections, and amplitude and phase of optimal RF are calculated for every imaging section as described above, the $B_1$ non-uniformity reducing effect can be maximized for each imaging section, but imaging time is extended.

According to this embodiment, in order to avoid this extension of the total imaging time, $B_1$ distributions are measured for a predetermined number of sections of a predetermined direction, regardless of the number and direction of the sections to be imaged. Then, from the measured $B_1$ distributions of the sections, the optimal radio frequency magnetic field conditions for each imaging section are determined by calculation. This embodiment will be explained below by exemplifying a case where the optimal radio frequency magnetic field conditions are optimal amplitude and phase of RF transmitted from each channel.

Figure 6:
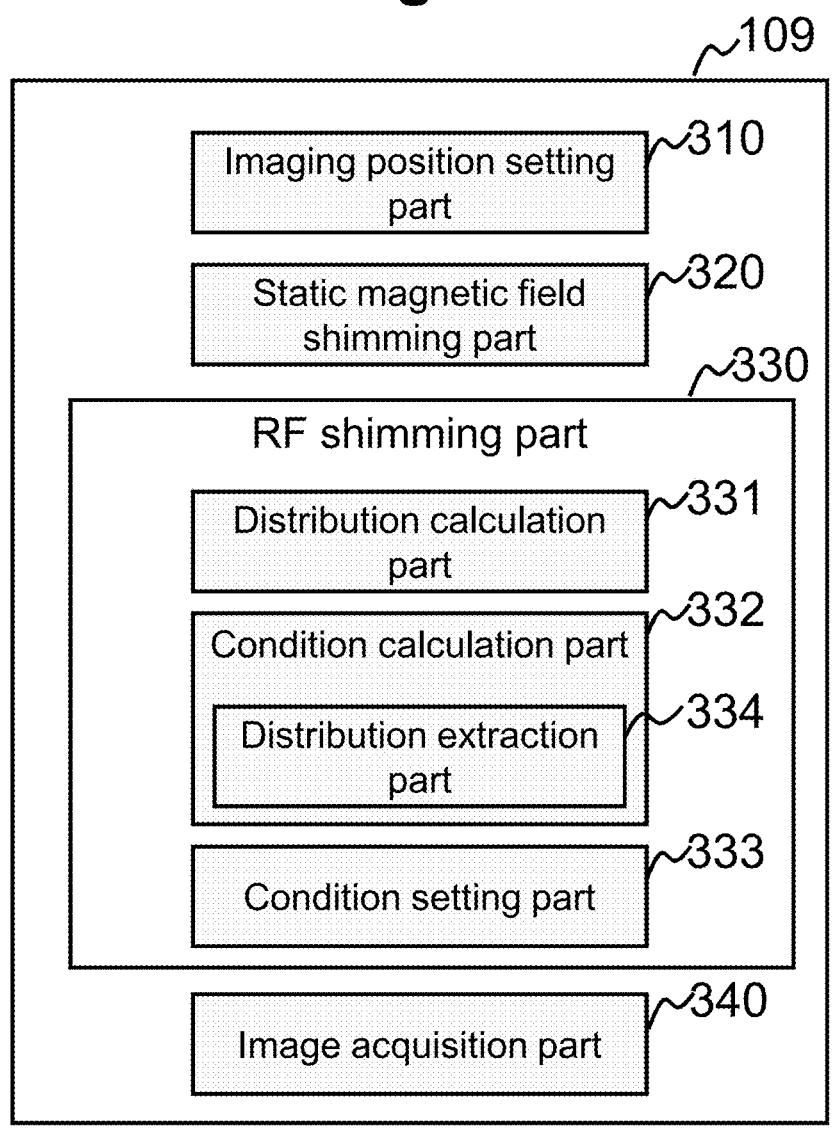
FIG. 6 is a functional block diagram of the calculation part according to the first embodiment.

FIG. 6 is a functional block diagram of the computer 109 of this embodiment for realizing the above operation. As shown in this drawing, the computer 109 according to this embodiment is provided with an imaging position setting part 310, a static magnetic field shimming part 320, an RF shimming part 330, and a image acquisition part 340. The functions of the computer 109 are realized by CPU provided in the computer 109 by loading programs stored in the storage device 111 beforehand on a memory and executing them.

The imaging position setting part 310 performs a scout scan or the like before performing the image acquisition to determine position of imaging section, and determines parameters concerning the position determination. The parameters concerning the position determination include, for example, axis direction of images to be obtained in the image acquisition, number and positions of sections, and so forth. Then, it sets the determined parameters as imaging conditions used for the image acquisition. The processing executed by the imaging position setting part 310 is referred to as imaging position setting processing.

The static magnetic field shimming part 320 measures the static magnetic field distribution, and performs static magnetic field shimming processing in which parameters concerning adjustment of uniformity of static magnetic field are determined so that the static magnetic field becomes as uniform as possible. Then, it sets the determined parameters as imaging conditions used for the image acquisition. The processing performed by the static magnetic field shimming part 320 is referred to as static magnetic field shimming processing. When uniformity of the static magnetic field sufficient for the imaging is obtained without performing the static magnetic field shimming processing, it is not necessary to perform this processing. When the static magnetic field shimming processing is not performed, the static magnetic field shimming part 320 may not be provided. Hereafter, this embodiment will be explained for an example where the static magnetic field shimming processing is not performed.

The RF shimming part 330 determines parameters concerning the RF shimming (radio frequency magnetic field conditions) for every imaging section. According to this embodiment, amplitude and phase of optimal RF to be transmitted from each channel are calculated as the radio frequency magnetic field conditions for every imaging section. And the calculated radio frequency magnetic field conditions are set as the imaging conditions used for the image acquisition. The processing performed by the RF shimming part 330 is called RF shimming processing. The details of the RF shimming processing according to this embodiment will be explained later.

The image acquisition part 340 carries out the image acquisition on the basis of the imaging conditions set in the imaging position setting part 310, the static magnetic field shimming part 320, and the RF shimming part 330.

Hereafter, the RF shimming processing performed by the RF shimming part 330 according to this embodiment will be explained. The RF shimming part 330 according to this embodiment is provided with a distribution calculation part 331 for calculating $B_1$ distribution (radio frequency magnetic field distribution) of a distribution measurement section perpendicular to a distribution measurement axis defined from the magnetic resonance signals beforehand, a condition calculation part 332 for calculating the radio frequency magnetic field condition for an arbitrary imaging section by using the obtained $B_1$ distribution, and a condition setting part 333 for setting the obtained radio frequency magnetic field condition as an imaging condition used for the image acquisition. In this explanation, values of amplitude and phase of RF optimal for an imaging section calculated as the radio frequency magnetic field conditions are set as parameter values of the RF pulse in the sequencer 104. According to this embodiment, setting is performed so that a voltage of the calculated amplitude and phase is transmitted to the feeding point 201 of each channel of the transmission coil 114.

Further, the condition calculation part 332 is provided with a distribution extraction part 334 for extracting $B_1$ distribution ($B_1$ values) of a region containing a line of intersection of the imaging section and the distribution measurement section (henceforth referred to as crossing region) from the $B_1$ distribution of the distribution measurement section. The crossing region is a region having predetermined widths for the directions perpendicular to the measurement axis direction and the imaging section.

Hereafter, the details of the processings performed by the distribution calculation part 331 and the condition calculation part 332 will be explained with reference to a specific example.

First, the details of the processing performed by the distribution calculation part 331 will be explained. The distribution calculation part 331 performs measurement for obtaining the $B_1$ distribution in the imaging region, and calculates the $B_1$ distribution for every channel for a predetermined distribution measurement section from the measured results. The $B_1$ distribution in the imaging region is measured by executing a predetermined sequence. Further, the measurement axis of the distribution measurement section is desirably set to be a direction along which change of the $B_1$ distribution is small. Alternatively, it is desirably set to be a direction along which shape change of the subject is smallest.

For example, when the subject 103 is a human, and the birdcage coil shown in FIG. 2 is used as the transmission coil 114, it is desirable to use an AX section as the distribution measurement section, and the z-axis as the measurement axis. This is because of the following reasons.

As for the current distribution in each rung linearly extending along the z-axis direction in the birdcage coil having the shape shown in FIG. 2, electric current change along the z-axis direction is small, and the current distribution is substantially uniform. Therefore, if a birdcage coil of such a shape is used, distribution of the generated magnetic field for the z-axis direction also becomes substantially uniform, and it is considered that change of $B_1$ along the z-axis direction is also small.

From the $B_1$ distributions in the SAG section (yz-plane) and the COR section (xz-plane) shown in FIGS. 3B and 3C, it can be seen that change of $B_1$ along the z-axis direction is comparatively small. On the other hand, as shown in FIG. 3A, the $B_1$ distribution significantly changes in the AX section (xy-plane). Therefore, it can be said that, considering three-dimensional distribution of $B_1$ in the imaging region, $B_1$ change for the z-axis direction is smaller than the $B_1$ changes for the x- and y-axis directions.

Although the $B_1$ distribution also significantly depends on the shape of the imaging section, when shape change of the imaging section is small along the z-axis direction, substantially the same $B_1$ distribution is observed in a plurality of AX sections of different z coordinate values. For example, when the imaging region is a pelvis region or epigastric region, change of the sectional shape along the z-axis direction is comparatively small, and therefore the $B_1$ distribution shows similar tendency at any z coordinate value.

For the above reasons, when the subject 103 is a human, and the birdcage coil shown in FIG. 2 is used as the transmission coil 114, for example, the z-axis direction (direction perpendicular to AX section) is the direction for which change of the $B_1$ distribution is the smallest, and the shape change of the subject 103 is the smallest, and it is desirable as the measurement axis direction.

Further, the distribution measurement section for which the measurement is performed is desirably set within the imaging region in which all the imaging sections are included. In the explanation of this embodiment, the number of the distribution measurement sections to be measured is henceforth defined to be N (N is an integer of 1 or larger). In a specific example, the measurement axis direction is set to be the AX direction, and the number of the distribution measurement sections N is set to be 3.

Figure 7:
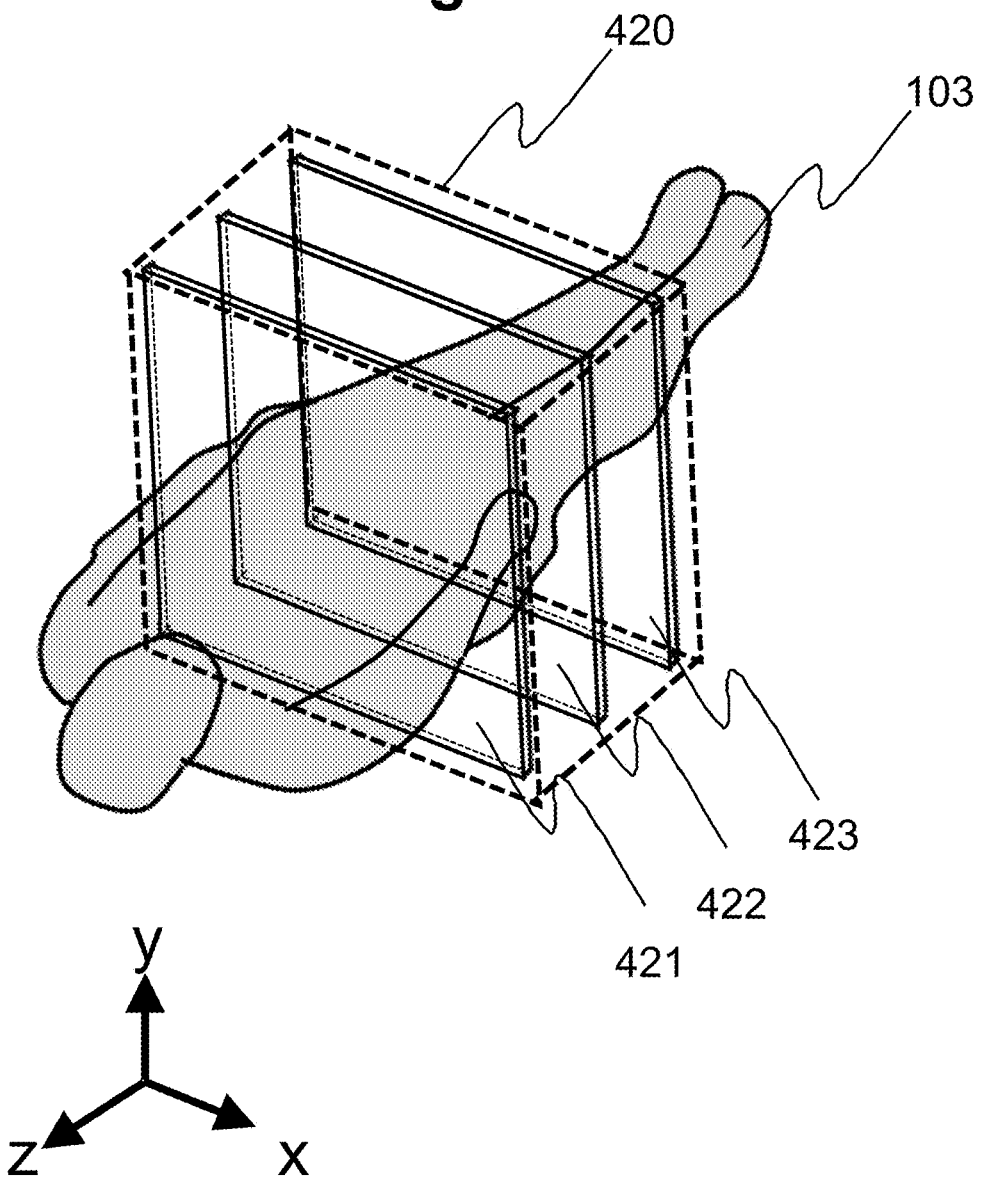
FIG. 7 is an explanatory drawing for explaining the imaging region and $B_1$ distribution measurement section according to the first embodiment.

For example, for a case where a plurality of imaging sections are set for each of the y-axis direction (AX sections), x-axis direction (SAG sections), and y-axis direction (COR sections) as shown in FIGS. 5A to 5C, the distribution measurement section is set within the imaging region 420 shown in FIG. 7, which includes the imaging sections 411, 412, and 413. For example, when the measurement axis is set to be the AX direction, and the number of the distribution measurement sections N is set to be 3, the distribution measurement sections are set at the both end positions 421 and 423, and the center position 422 of the imaging region 420 for the AX direction, as shown in FIG. 7.

For example, if imaging of a pelvis region is supposed, FOV (field of view) for the z-axis direction of the images of the SAG and COR directions is set to be 300 mm, and the center of the region 420 for the z-axis direction is set as the starting point, the $B_1$ distributions are measured for the distribution measurement sections 421, 422 and 423 passing through the three points where z=−150 mm, 0 mm, and 150 mm. For this measurement, FOV of the distribution measurement sections is defined to be about 300 to 500 mm, and the slice width is defined to be about 5 to 20 mm.

The measurement of $B_1$ distributions of a plurality of the distribution measurement sections is performed by using, for example, the multi-slice method or the like.

Hereafter, the details of the processing performed by the condition calculation part 332 will be explained. The condition calculation part 332 calculates the optimal radio frequency magnetic field conditions by different procedures for the imaging section perpendicular to the measurement axis and the other imaging sections.

First, the method for the calculation of the optimal radio frequency magnetic field conditions, which is performed by the condition calculation part 332, for the case where the imaging section is perpendicular to the measurement axis, i.e., the imaging section is parallel to the distribution measurement section, will be explained. For this calculation, the condition calculation part 332 first calculates the optimal radio frequency magnetic field for each distribution measurement section for every channel, and registers the calculation results at, for example, the storage device 111 or the like. The optimal radio frequency magnetic field conditions for each distribution measurement section for every channel can be calculated in accordance with the following equation (2) by using $B_1$ distribution of each distribution measurement section.

$$Bx=m \qquad (2)$$

In the equation, B is a matrix representing $B_1$ distributions of the channels, m is a matrix representing ideal $B_1$ distributions, and x is the optimal radio frequency magnetic field conditions desired to be obtained (amplitude and phase of RF in this case). The matrix m includes, for example, the same values for all the elements supposing ideal $B_1$ distributions. The aforementioned equation (2) is solved by using, for example, the least square method, to calculate the values of x. The obtained radio frequency magnetic field conditions are the optimal radio frequency magnetic field conditions.

For example, when $B_1$ distribution of each channel consists of data of 1000 points, and the number of the channels is 2, B is a matrix of 1000×2. Further, x is a matrix of 2×1, and m is a matrix of 1000×1. For example, when amplitude and phase of RF are calculated as the radio frequency magnetic field conditions for the channel number of 2, and the distribution measurement section number N of 3, three sets in total of the values of amplitude and phases (A1, A2, Φ1, Φ2) are calculated.

After the optimal radio frequency magnetic field conditions for each distribution measurement section are obtained, the condition calculation part 332 extracts two or more of the distribution measurement sections from the distribution measurement sections, and calculates the optimal radio frequency magnetic field condition for the imaging section by interpolation. For example, when the interpolation is performed by using two of the distribution measurement sections, it is desirable to use the radio frequency magnetic field conditions for the distribution measurement sections on the both sides of the imaging section.

Figure 8:
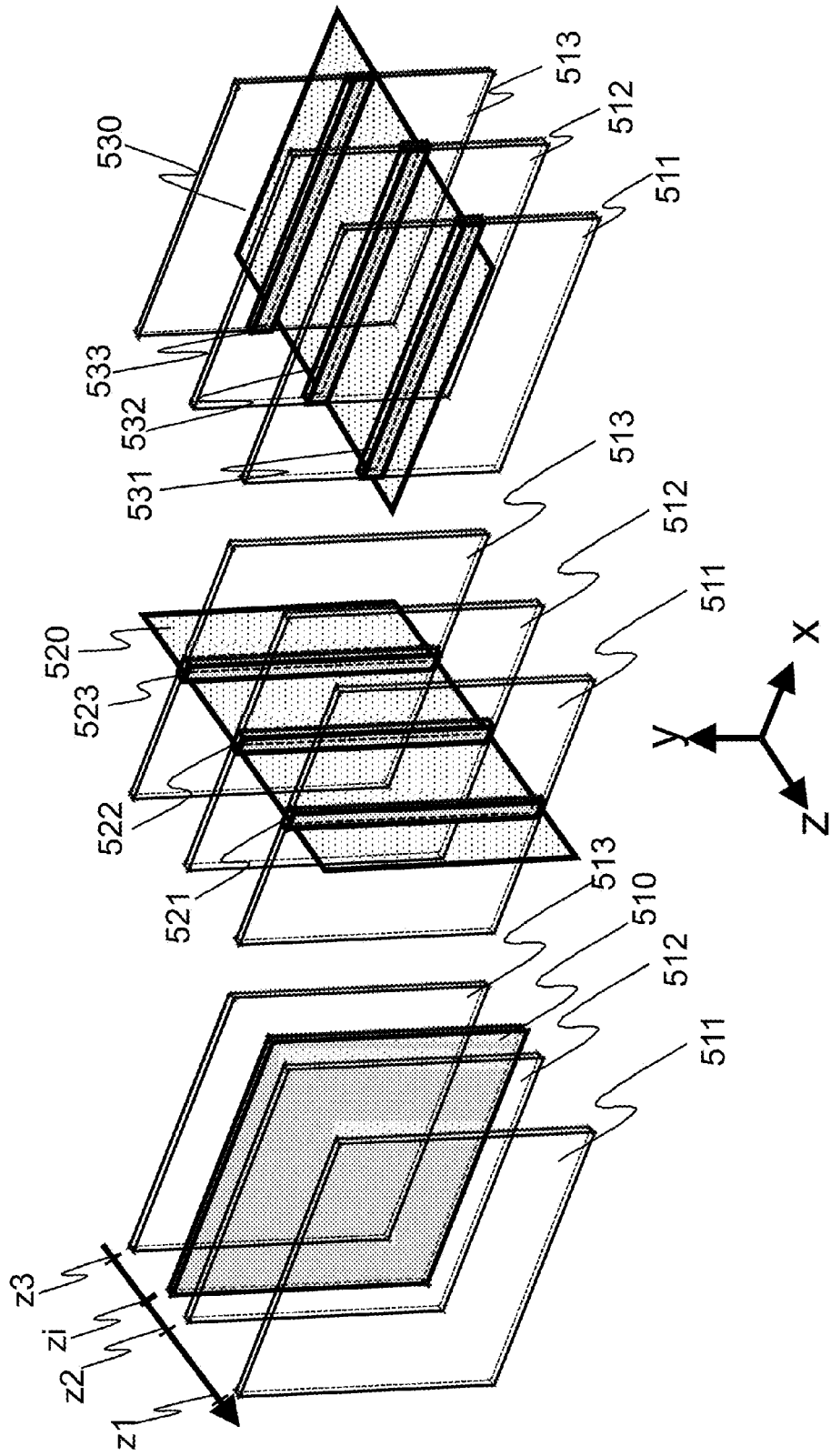
FIG. 8A is an explanatory drawing for explaining the method for calculating an optimal radio frequency magnetic field condition for an imaging section according to the first embodiment, which is for the case where the imaging section is an AX section.
FIG. 8B is an explanatory drawing for explaining the method for calculating an optimal radio frequency magnetic field condition for an imaging section according to the first embodiment, which is for the case where the imaging section is a SAG section.
FIG. 8C is an explanatory drawing for explaining the method for calculating an optimal radio frequency magnetic field condition for an imaging section according to the first embodiment, which is for the case where the imaging section is a COR section.

The method for calculating the radio frequency magnetic field condition for the imaging section by interpolation will be explained below with reference to a specific example. In this example, as shown in FIG. 8A, the distribution measurement sections are three sections 511, 512, and 513 of the AX direction (z-axis direction), the imaging section 510 is of the same direction and locates between the distribution measurement section 511 and the distribution measurement section 512, and the radio frequency magnetic field conditions are amplitude and phase of RF. Further, the z coordinate values of the measurement sections 511, 512, and 513 are set to be z1, z2, and z3 (z1≤z2≤z3), respectively, and the z coordinate value of the imaging section 510 is set to be zi (z1≤zi≤z2).

Changes of the sectional shape of the subject, amplitude and phase of optimal RF along the z-axis direction are considered to be substantially linear. Therefore, the value $A1_{zi}$ of the amplitude A1 of the optimal RF for the channel 1 for the imaging section 510 can be calculated in accordance with, for example, the following equation (3).

[Equation 3]

$$A1_{zi} = A1_{z1} \cdot \frac{z2-zi}{z2-z1} + A1_{z2} \cdot \frac{zi-z1}{z2-z1} \qquad (3)$$

In the equation, $A1_{z1}$ and $A1_{z2}$ are amplitudes of the optimal RF for the channel 1 of the measurement sections 511 and 512, respectively.

The value $A2_{zi}$ of the amplitude $A2$ of the optimal RF for the channel 2 for the imaging section is calculated in accordance with the aforementioned equation (3) by using amplitudes of the optimal RF for the channel 2 of the measurement sections 511 and 512, $A2_{z1}$ and $A2_{z2}$, instead of $A1_{z1}$ and $A1_{z2}$. Further, the phase $\Phi1_{zi}$ of the optimal RF for the channel 1 is calculated in accordance with the aforementioned equation (3) by using phases of the optimal RF for the channel 1 for the measurement sections 511 and 512, $\Phi1_{z1}$ and $\Phi1_{z2}$, instead of $A1_{z1}$ and $A1_{z2}$. The phase $\Phi2_{zi}$ of the optimal RF for the channel 2 is calculated in accordance with the aforementioned equation (3) by using phases of the optimal RF for the channel 2 for the measurement sections 511 and 512, $\Phi2_{z1}$ and $\Phi2_{z2}$, instead of $A1_{z1}$ and $A1_{z2}$.

When the imaging section coincides with any of the distribution measurement sections (when zi is equal to z1, z2, or z3), the optimal radio frequency magnetic field condition for the coinciding distribution measurement section is used as the radio frequency magnetic field condition for the imaging section as it is. These may also be calculated by using the equation (3).

Hereafter, the method for the calculation of the optimal radio frequency magnetic field conditions, which is performed by the condition calculation part 332, for the case where the imaging section is perpendicular to an axis other than the measurement axis, i.e., the imaging section is not parallel to the distribution measurement section, will be explained. In this case, the condition calculation part 332 first makes the distribution extraction part 334 extract the $B_1$ distributions of the crossing regions of the imaging section and the distribution measurement sections for every channel. Then, the condition calculation part 332 calculates the optimal radio frequency magnetic field condition for the imaging section from the obtained $B_1$ distributions of the crossing regions for every channel by using the aforementioned equation (2). In this calculation, the condition calculation part 332 uses a matrix representing $B_1$ distributions of the crossing regions for the channels as B in the aforementioned equation (2).

For the above calculation, the width of the crossing region extracted by the distribution extraction part 334 for the direction perpendicular to the imaging section is desirably about 10 to 80 mm. This is because, if the width of the crossing region is too small, the number of the $B_1$ values to be extracted decreases, and becomes insufficient for calculating amplitude and phase of the optimal RF, but to the contrary, if the length of the crossing region is too large, the positional information is degraded. The spatial change of the $B_1$ distribution mainly depends on the RF wavelength, and as the wavelength becomes smaller, the spatial change becomes more significant. Therefore, for a shorter wavelength, the width must be set to be a smaller width.

The method for calculating the optimal radio frequency magnetic field conditions for the case where the imaging section is not parallel to the distribution measurement section will be explained below with reference to a specific example. The distribution measurement section is defined to consist of three sections 511, 512, and 513 of the AX direction, as in the case shown in FIG. 8A.

For example, as shown in FIG. 8B, the imaging section 520 is defined to be an SAG section. In this case, the distribution extraction part 334 extracts $B_1$ values of only predetermined regions 521, 522, and 523 (crossing regions) from the $B_1$ distributions of the three distribution measurement sections 511, 512, and 513, as shown in FIG. 8B. The above crossing regions 521, 522, and 523 each include a line of intersection (broken lines shown in FIG. 8B) with the imaging section 520, which is an SAG section (section of the SAG α-axis) direction). For example, when the position of the imaging section 520 for the x-axis direction is 0 (x=0 mm), only the $B_1$ values of such regions (521, 522, 523) having a strip shape extending along the y-axis direction on both sides of the position where x=0 mm as shown in FIG. 8B are extracted. Then, the condition calculation part 332 calculates the optimal radio frequency magnetic field conditions from these $B_1$ values in accordance with the equation (2).

Further, as shown in FIG. 8C, the imaging section 530 is defined to be a COR section. In this case, the distribution extraction part 334 extracts $B_1$ values of only predetermined regions 531, 532, and 533 (crossing regions) from the $B_1$ distributions of the three distribution measurement sections 511, 512, and 513, as shown in FIG. 8C. The above crossing regions 531, 532, and 533 each include a line of intersection (broken lines shown in FIG. 8C) with the imaging section 530, which is a COR section (section of the COR (y-axis) direction). For example, when the position of the imaging section 530 for the y-axis direction is 0 (y=0 mm), only the $B_1$ values of such regions (531, 532, 533) having a strip shape extending along the x-axis direction on both sides of the position where y=0 mm as shown in FIG. 8C are extracted. Then, the condition calculation part 332 calculates the optimal radio frequency magnetic field conditions from these $B_1$ values in accordance with the equation (2).

Figure 9:
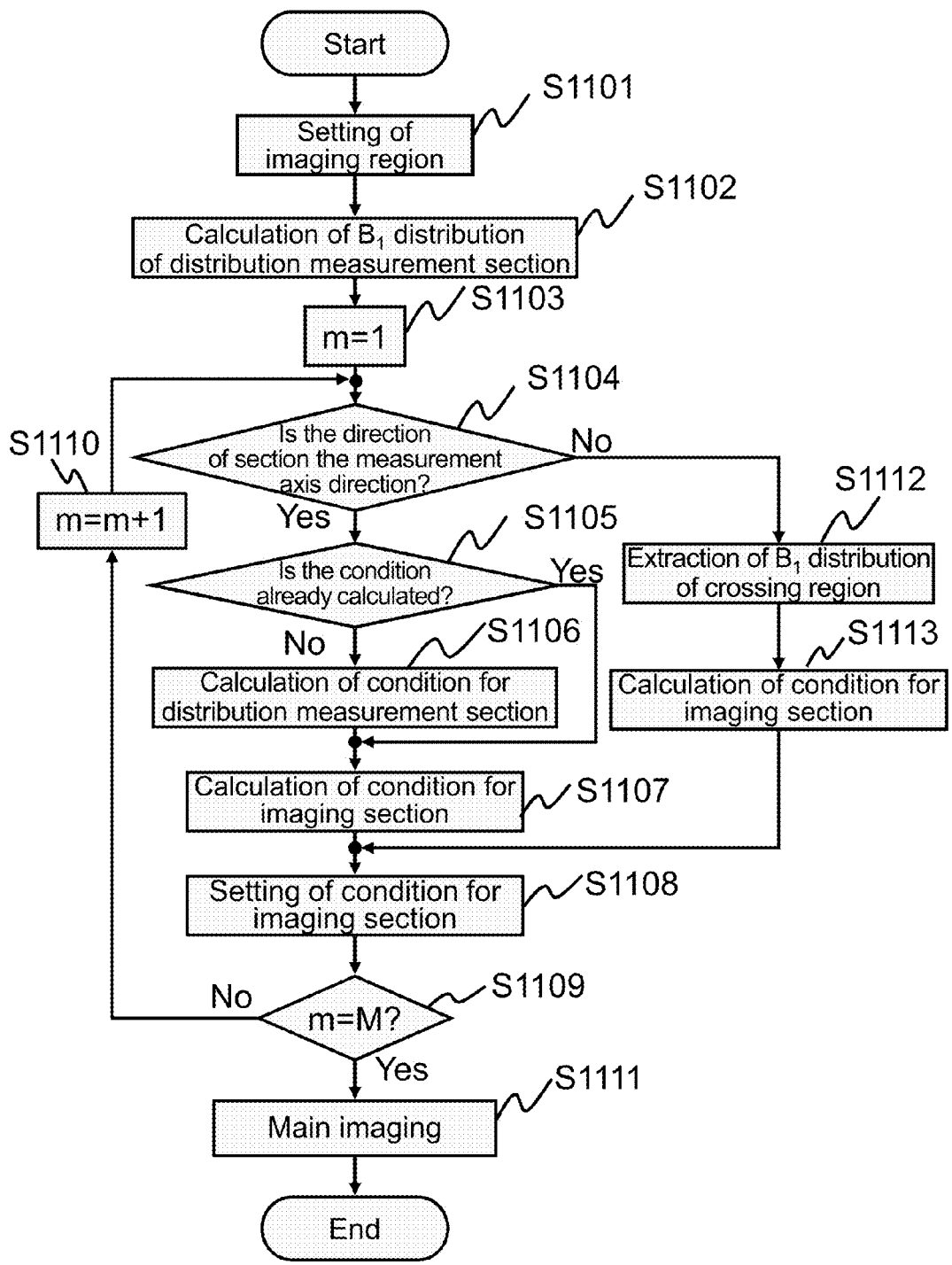
FIG. 9 is a flowchart of the imaging processing according to the first embodiment.

Hereafter, the flow of the imaging processing performed by the computer 109 according to this embodiment will be explained with reference to FIG. 9. FIG. 9 shows the process flow of the imaging processing according to this embodiment. In this example, the measurement axis direction is the AX direction, and the number of distribution measurement sections is N. Further, the number of imaging sections is M (M is an integer of 1 or larger).

First, the imaging position setting part 310 performs imaging region setting processing (Step S1101). Then, the distribution calculation part 331 performs $B_1$ distribution measurement, and calculates $B_1$ distributions of N of the distribution measurement sections of the AX direction (Step S1102).

In this calculation, the distribution calculation part 331 determines the imaging region for which $B_1$ distribution is measured with reference to parameters concerning the position of the image obtaining in the image acquisition calculated by the imaging position setting part 310.

Then, the RF shimming part 330 performs the RF shimming processing for every imaging section set by the imaging position setting part 310. In this processing, the condition calculation part 332 calculates the optimal radio frequency magnetic field conditions for every imaging section, and sets the radio frequency magnetic field conditions calculated by the condition setting part 333.

As the RF shimming processing, the RF shimming part 330 repeats the following processings a number of times corresponding to the total number of imaging sections, i.e., M times (Steps S1103, S1109, and S1110).

First, the condition calculation part 332 determines whether the direction of the m-th imaging section (m is an integer satisfying 1≤m≤M) of the object of the processing is the measurement axis direction or not (Step S1104). And if it is the measurement axis direction, the condition calculation part 332 determines whether the optimal radio frequency magnetic field conditions for the distribution measurement sections are already calculated or not (Step S1105). Whether they are already calculated or not is determined on the basis of, for example, whether the optimal radio frequency magnetic field conditions for the distribution measurement sections are registered at the storage device 111 or not.

When it is determined that they are not calculated yet in Step S1105, the condition calculation part 332 calculates the optimal radio frequency magnetic field conditions for the distribution measurement sections by using the aforementioned method, registers them at the storage device 111 (Step S1106), and calculates the optimal radio frequency magnetic field condition for the m-th imaging section according to the aforementioned method by using the calculated optimal radio frequency magnetic field conditions for each distribution measurement section (Step S1107). On the other hand, when it is determined that they are already calculated in Step S1105, the process moves to Step S1106, and the optimal radio frequency magnetic field condition for the m-th imaging section is calculated according to the aforementioned method by using the already calculated optimal radio frequency magnetic field conditions for each distribution measurement section.

The condition setting part 333 sets the calculated optimal radio frequency magnetic field condition as imaging condition for the m-th imaging section (Step S1108). And the condition setting part 333 determines whether the processing is finished for all the imaging sections or not (Step S1109), and if it is not finished, m is incremented by one (Step S1110), the process returns to Step S1104, and the processing is repeated.

When it is determined that the processing is finished for all the imaging sections in Step S1109, the RF shimming part 330 finishes the RF shimming processing, and the image acquisition part 340 performs the image acquisition (Step S1111).

On the other hand, when it is determined that the m-th imaging section of the object of the processing is not a section of the measurement axis direction in Step S1104, the condition calculation part 332 makes the distribution extraction part 334 extract $B_1$ distributions of the crossing regions of the m-th imaging section and the distribution measurement sections (Step S1112). And the condition calculation part 332 calculates the optimal radio frequency magnetic field condition for the m-th imaging section according to the aforementioned method from the extracted $B_1$ distributions (Step S1113). And the process moves to Step S1108.

The flow of the whole imaging processing including the RF shimming according to this embodiment was explained above.

An example of the experimental result of application of the RF shimming according to this embodiment to actual imaging of human will be shown below.

First, the result of application of the RF shimming according to this embodiment to a pelvis region is shown. Specific experimental conditions are described first. As the experimental apparatus, a 3T MRI apparatus was used. The imaging sections consisted of 5 AX sections, 7 SAG sections, and 3 COR sections. As the optimal radio frequency magnetic field conditions, amplitude and phase of RF were calculated.

The intervals of the AX sections were 75 mm along the z-axis direction, the intervals of the SAG sections were 40 mm along the x-axis direction, and the intervals of the COR sections were 40 mm along the y-axis direction. The position on the z-axis of the center section among the 5 AX sections along the AX direction was 0 mm, and the positions of the other four sections on the z-axis were −150 mm, −75 mm, 75 mm, and 150 mm, respectively. The position on the x-axis of the center section among the 7 SAG sections along the SAG direction was 0 mm, and the positions of the other 6 sections on the x-axis were −120 mm, −80 mm, −40 mm, 40 mm, 80 mm, and 120 mm, respectively. Further, the position on the y-axis of the center section among the 3 COR sections along the COR direction was 0 mm, and the positions of the other 2 sections on the y-axis were −40 mm and 40 mm, respectively.

Figure 10A:
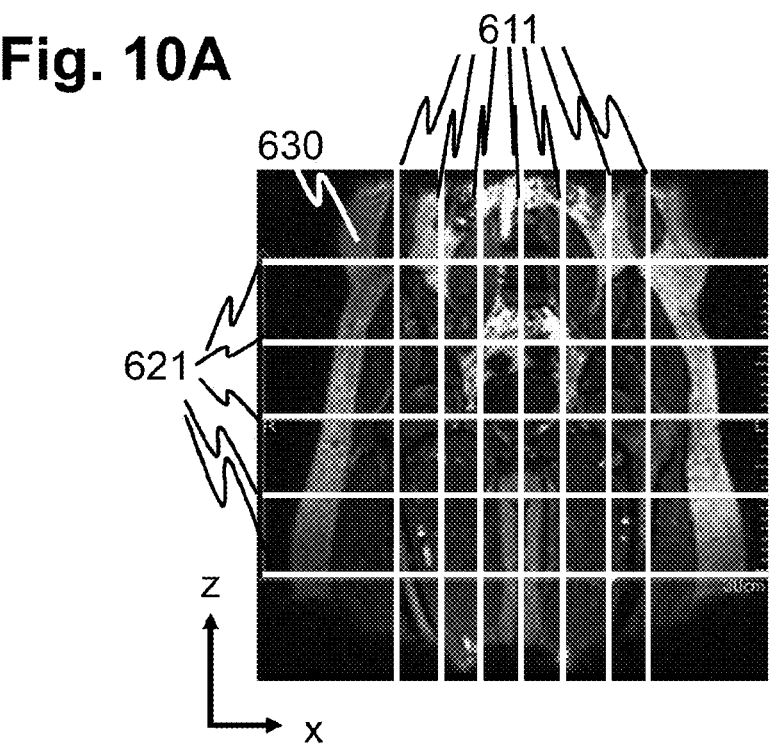
FIG. 10A is an explanatory drawing for explaining a specific example of the first embodiment, which shows set AX section positions and SAG section positions on a COR image of a pelvis region.

FIG. 10A is a drawing where set AX section positions 611 and SAG section positions 621 are shown on a COR image 630 of a pelvis region. In order to confirm the effect of this embodiment in the whole pelvis region, these imaging section positions were set.

In the experiment, in order to verify the effect of this embodiment, three kinds of the methods for calculating amplitude and phase of RF were performed and compared. The compared methods are the following three kinds of methods: (Method 1) $B_1$ distributions were measured for all the imaging sections (5 AX sections, 7 SAG sections, 3 COR sections, 15 sections in total), and amplitude and phase of the optimal RF are calculated for every imaging section, (Method 2) amplitude and phase of the optimal RF are calculated for every imaging section from $B_1$ distribution of only one AX section at the center along the AX direction (this method corresponds to the method of this embodiment where the distribution measurement section consists of one section), and (Method 3) amplitude and phase of the optimal RF are calculated for every imaging section from $B_1$ distributions of three AX sections (this method corresponds to the method of this embodiment where the distribution measurement sections consist of three sections).

The specific processing method of Method 3 will be explained below. The distribution measurement sections consisted of the AX sections at the positions of −150 mm, 0 mm, and 150 mm. That is, the $B_1$ distribution was measured at the positions where z=−150 mm, 0 mm, and 150 mm.

First, the method for calculating amplitude and phase of the optimal RF for 5 AX sections will be explained. For the imaging sections at the positions where z=150 mm, 0 mm, and 150 mm, amplitude and phase of RF were calculated from the $B_1$ distribution measured at each coordinate position. Further, for an imaging section position where z=75 mm, amplitude and phase of the optimal RF were calculated by interpolation using the values of amplitude and phase of RF calculated from the $B_1$ distributions of the two distribution measurement sections at the positions where z=0 mm and z=150 mm. For an imaging section position where z=−75 mm, amplitude and phase of the optimal RF were calculated by interpolation using the values of amplitude and phase of RF calculated from the $B_1$ distributions of the two distribution measurement sections at the positions where z=0 mm and z=−150 mm.

Figure 10B:
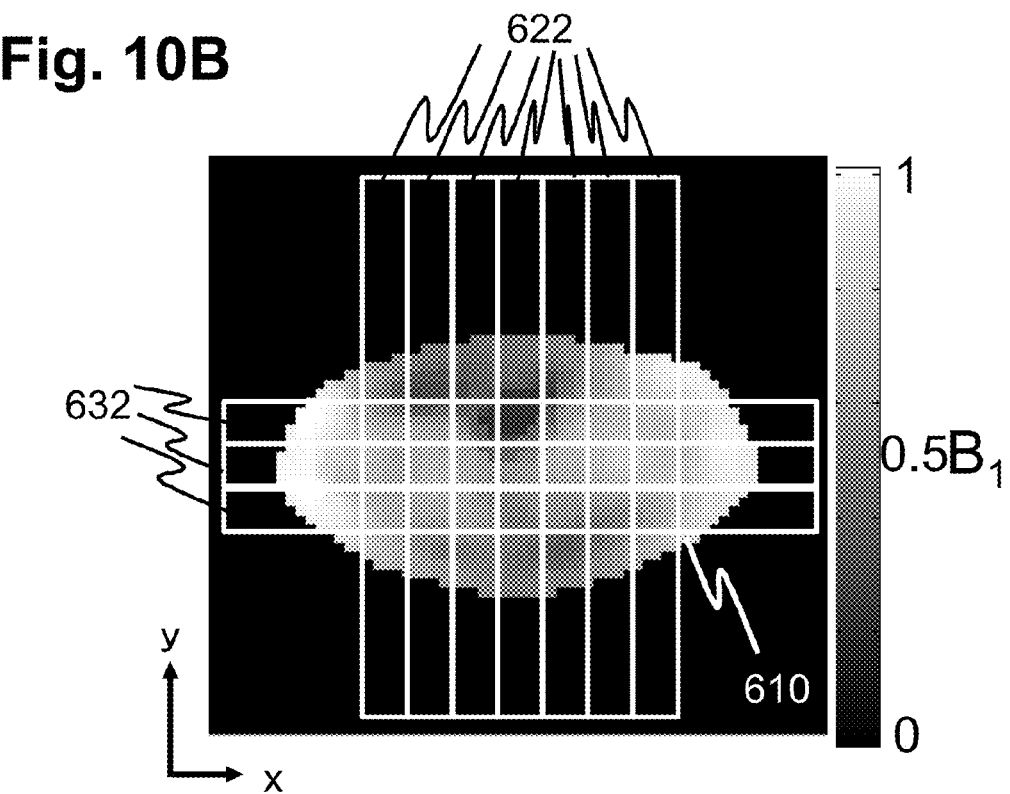
FIG. 10B is an explanatory drawing for explaining a specific example of the first embodiment, which shows crossing regions of the SAG and COR directions on an AX image of the pelvis region.

The method for calculating amplitude and phase of the optimal RF for 7 SAG sections will be explained below. FIG. 10B shows an image 610 of an AX section of a human pelvis region, crossing regions 622 of a strip shape around each imaging section position along the SAG direction, and crossing regions 632 around imaging section positions of three imaging sections along the COR direction. The image 610 is an image showing the $B_1$ distribution of the distribution measurement section.

The amplitude and phase of the optimal RF for the center section of the SAG direction (section at the position where x=0 mm) were calculated by using $B_1$ values extracted from the center crossing region 622 among the crossing regions 622 as B in the aforementioned equation (2), and the calculation was performed. For the other imaging sections, the amplitude and phase of the optimal RF were similarly calculated by using extracted $B_1$ values of the crossing region 622 around the corresponding imaging section as B in the aforementioned equation (2), and the calculation was performed.

Supposing the image acquisition, the slice thickness is about several millimeters, but the length for the x-axis direction of the crossing region 622 of the SAG direction shown in FIG. 10B was set to be 40 mm. If the width of the crossing region 622 of the SAG direction for the x-axis direction is too small, the number of the $B_1$ values to be extracted decreases, and may be insufficient for calculating amplitude and phase of the optimal RF. To the contrary, if the length of the crossing region 622 of the SAG direction for the x-axis direction is too large, the positional information of the SAG section is degraded. Therefore, the length of the crossing region 622 for the x-axis direction is desirably about 10 to 800 mm.

The method for calculating amplitude and phase of the optimal RF for the three COR sections was the same as that used for the SAG sections. That is, amplitude and phase of the optimal RF are calculated by using the $B_1$ distributions of the crossing regions 632 having a strip shape of which center position is each corresponding imaging section.

For the above three kinds of methods, the $B_1$ non-uniformity reducing effect was confirmed. For this purpose, non-uniformity of $B_1$ distribution was evaluated by using a quantitative index $U_{SD}$ represented by the following equation (4).

[Equation 4]

$$U_{SD} = \frac{\sigma(B_1)}{m(B_1)} \quad (4)$$

$m(B_1)$ and $\sigma(B_1)$ represent average and standard deviation of $B_1$, respectively. The uniformity index $U_{SD}$ represented by the equation (4) is a value obtained by dividing the standard deviation with the average. A smaller value of this $U_{SD}$ represents smaller dispersion of $B_1$. Therefore, a smaller value of $U_{SD}$ represents higher. $B_1$ uniformity.

Figure 11A:
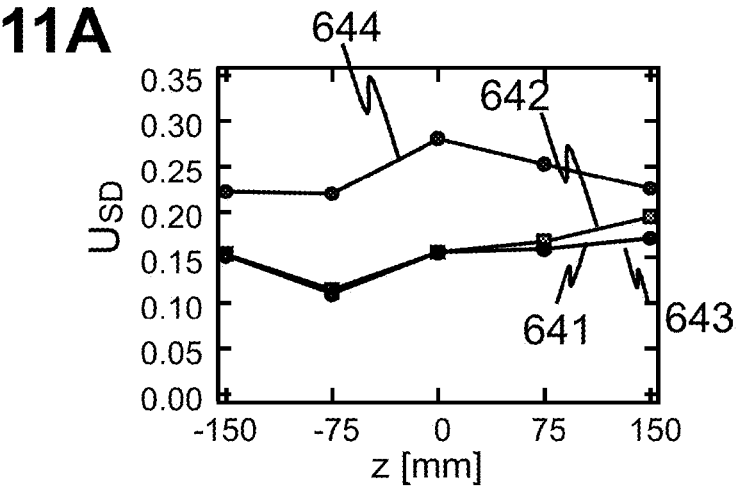
FIG. 11A is a graph of $B_1$ uniformity index for the case where the imaging section is an AX section of the pelvis region.
Figure 11B:
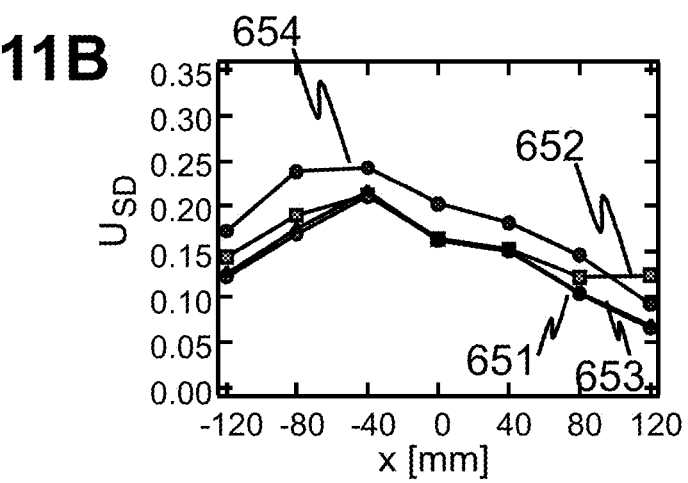
FIG. 11B is a graph of $B_1$ uniformity index for the case where the imaging section is an SAG section of the pelvis region.
Figure 11C:
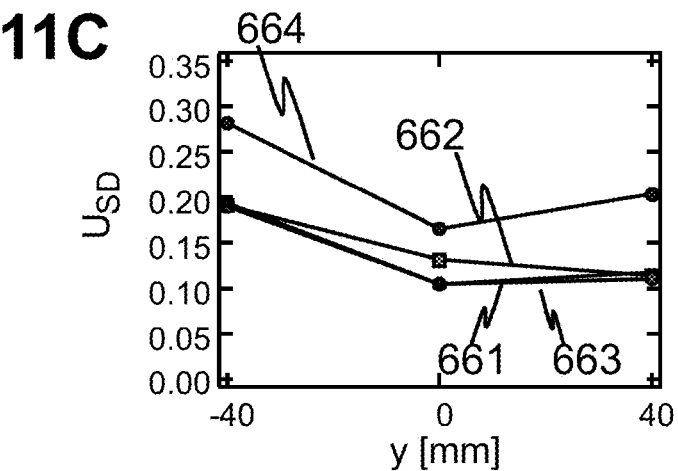
FIG. 11C is a graph of $B_1$ uniformity index for the case where the imaging section is a COR section of the pelvis region.

The uniformity index $U_{SD}$ values for the imaging sections of each direction obtained with the aforementioned methods are shown in FIG. 11. FIG. 11A shows values of the uniformity index $U_{SD}$ obtained by the aforementioned methods for the imaging sections of the AX direction in the pelvis region, FIG. 11B shows the same for the imaging sections of the SAG direction, and FIG. 11C shows the same for the imaging sections of the COR direction. The values of the uniformity index $U_{SD}$ obtained by QD irradiation without using the RF shimming are also shown. In the graphs, the vertical axis indicates the value of $U_{SD}$, and the horizontal axis indicates the position for each direction. In FIG. 11A, the results (uniformity index) obtained with Method 1 are represented with a line 641, the results (uniformity index) obtained with Method 2 are represented with a line 642, the results (uniformity index) obtained with Method 3 are represented with a line 643, and the results obtained with QD irradiation without using the RF shimming are represented with a line 644. Similarly, the same are represented with lines 651, 652, 653, and 654 in FIG. 11B, and with lines 661, 662, 663, and 664 in FIG. 11C, respectively.

As shown in FIG. 11A, in the case of the imaging sections of the AX direction, $U_{SD}$ values obtained with any of Method 1 (641), Method 2 (642), and Method 3 (643) were smaller than those obtained with the QD irradiation (644), and thus it can be seen that the $B_1$ non-uniformity was reduced. More precisely, it can be seen that the value of $U_{SD}$ obtained with Method 2 became larger for the imaging section at the position where z=150 mm compared with the values obtained with Method 1 or 3, and thus the $B_1$ non-uniformity reducing effect was smaller. It is considered that this is a result of using amplitude and phase of RF calculated from only the $B_1$ distribution of the center AX section (z=0 mm). On the other hand, with Methods 1 and 3, substantially the same values of $U_{SD}$ were obtained for all the imaging sections, and it was demonstrated that substantially the same $B_1$ non-uniformity reducing effect can be obtained with Methods 1 and 3.

The same tendency as that observed for the AX sections was also observed for the SAG sections and COR sections. As shown in FIGS. 11B and 11C, the value of $U_{SD}$ obtained with Method 2 became large for a part of the imaging sections, and thus the $B_1$ non-uniformity reducing effect was not sufficiently obtained. However, substantially the same values of $U_{SD}$ were obtained for all the imaging sections with Methods 1 and 3. Therefore, it was demonstrated that substantially the same $B_1$ non-uniformity reducing effect can be obtained with Methods 1 and 3.

With Method 1, the $B_1$ distribution measurement requires much time, but the $B_1$ distributions are measured for all the imaging sections themselves, and therefore amplitude and phase of the optimal RF can be calculated for all the imaging sections. Therefore, it can be said that the maximum $B_1$ non-uniformity reducing effect can be realized with Method 1. With Method 2, the $B_1$ distribution measurement time is as short as that for one section, but the obtained amplitude and phase of one RF are applied to all the 15 imaging sections. Therefore, the $B_1$ non-uniformity reducing effect may become small. However, the value of $U_{SD}$ became markedly smaller that that obtained with the QD irradiation (without RF shimming), and the uniformity of $B_1$ increased. Further, with Method 3, the $B_1$ distribution measurement time was short, and substantially the same degree of the $B_1$ non-uniformity reducing effect as that obtained with Method 1 was obtained.

On the basis of the above examination results, it was demonstrated that, when the imaging region is a pelvis region, substantially the same degree of the $B_1$ non-uniformity reducing effect as that obtained with Method 1, which provides the maximum $B_1$ non-uniformity reducing effect, can be obtained with Method 3, which is the method according to this embodiment. Therefore, it was demonstrated that the $B_1$ non-uniformity reducing effect of RF shimming can be maximized for all the imaging sections by the method according to this embodiment. Thus, the usefulness of the method of this embodiment (Method 3) was demonstrated.

The results of application of the RF shimming according to this embodiment to a cervical vertebra region will be shown below. A cervical vertebra region shows larger change of the AX sectional shape along the z-axis direction compared with a pelvis region. Usefulness of this embodiment for such a region showing large shape change was examined. In this examination, a 3T MRI apparatus was used as the experimental apparatus, and the optimal radio frequency magnetic field conditions to be calculated were amplitude and phase of RF, as is the aforementioned experiment for the pelvis region. The effect of this embodiment was confirmed for 9 AX sections, 5 SAG sections, and 3 COR sections. The intervals of the AX sections were 30 mm along the z-axis direction, the intervals of the SAG sections were 25 mm along the x-axis direction, and the intervals of the COR sections were 25 mm along the y-axis direction. The position on each axis of the center section for each direction was 0 mm.

Figure 12:
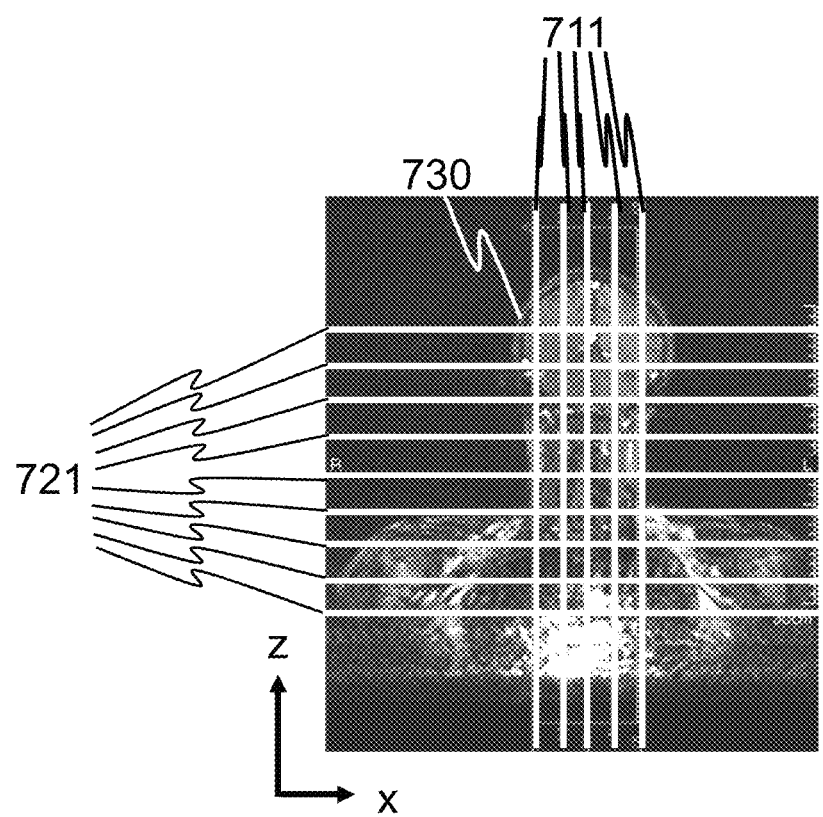
FIG. 12 is an explanatory drawing for explaining a specific example of the first embodiment, which shows section positions for the AX and SAG directions on a COR image of a cervical vertebra region.

FIG. 12 is a drawing where set AX section positions 711 and SAG section positions 721 are shown on a COR image 730 of a cervical vertebra region. In order to confirm the effect of this embodiment in the whole cervical vertebra, these imaging section positions were set. In Method 3, the distribution of $B_1$ was measured for three distribution measurement sections of the AX direction at positions of −120 mm, 0 mm, and 120 mm.

Figure 13A:
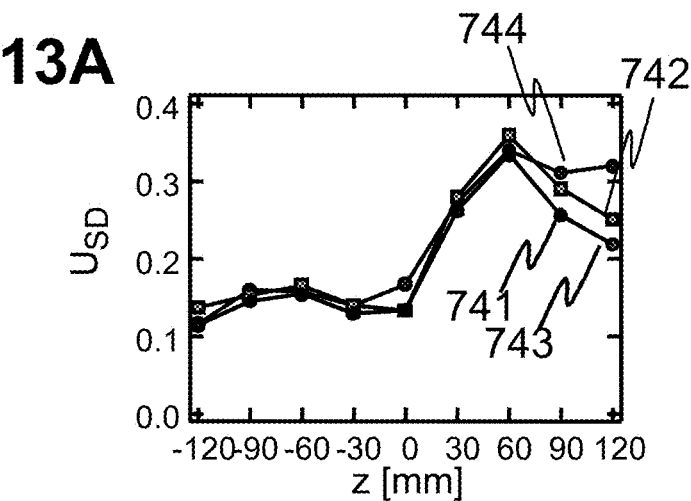
FIG. 13A is a graph of $B_1$ uniformity index for the case where the imaging section is an AX section of a cervical vertebra region.
Figure 13B:
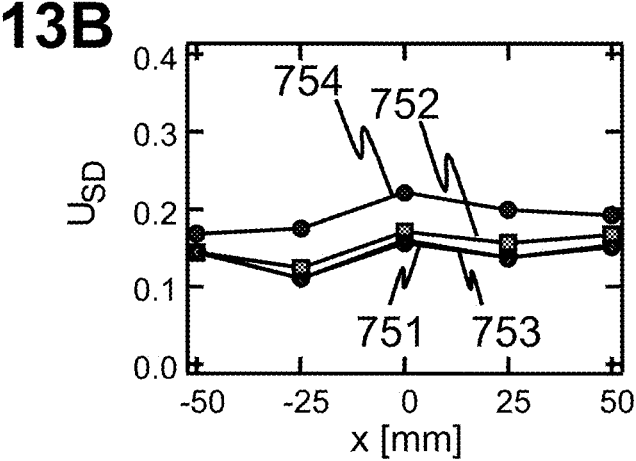
FIG. 13B is a graph of $B_1$ uniformity index for the case where the imaging section is an SAG section of a cervical vertebra region.
Figure 13C:
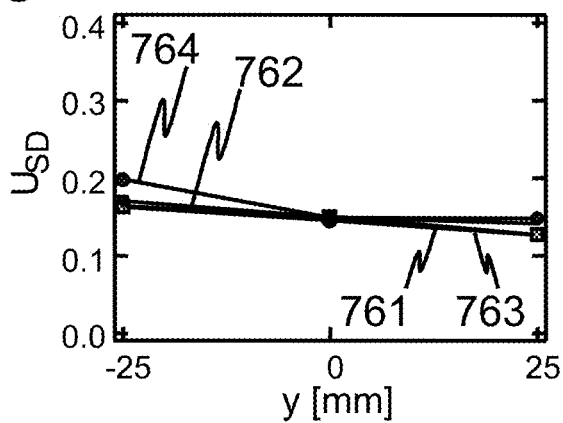
FIG. 13C is a graph of $B_1$ uniformity index for the case where the imaging section is a COR section of a cervical vertebra region.

The uniformity index $U_{SD}$ values for the imaging sections of each direction obtained with the aforementioned methods are shown in FIG. 13. FIG. 13A shows values of the uniformity index $U_{SD}$ obtained by the aforementioned methods for the imaging sections of the AX direction in the cervical vertebra region, FIG. 13B shows the same for the imaging sections of the SAG direction, and FIG. 13C shows the same for the imaging sections of the COR direction. In FIG. 13A, the results obtained with the methods are represented with lines 741, 742, and 743, respectively, and the same are represented with lines 751, 752, and 753 in FIG. 13B, and with lines 761, 762, and 763 in FIG. 13C, respectively. The uniformity index $U_{SD}$ values obtained with QD irradiation without using the RF shimming are also shown with lines 744, 754, and 764, respectively.

As shown in FIG. 13A, in the case of the imaging sections of the AX direction, $U_{SD}$ values obtained with any of Method 1 (741), Method 2 (742), and Method 3 (743) were smaller than those obtained with the QD irradiation (744), and thus it can be seen that the $B_1$ non-uniformity was reduced. More precisely, it can be seen that the value of $U_{SD}$ obtained with Method 2 became larger for the imaging section at the positions other than the position where z=0 mm compared with the values obtained with Method 1 or 3, and thus the $B_1$ non-uniformity reducing effect was smaller. On the other hand, with Methods 1 and 3, substantially the same values of $U_{SD}$ were obtained for all the imaging sections, and it can be seen that substantially the same $B_1$ non-uniformity reducing effect can be obtained with Methods 1 and 3.

The same tendency was also observed for the imaging sections of the SAG and COR directions as shown in FIGS. 13B and 13C. That is, the value of $U_{SD}$ obtained with Method 2 became large for a part of the imaging sections, and thus the $B_1$ non-uniformity reducing effect was not sufficiently obtained. However, substantially the same values of $U_{SD}$ were obtained for all the imaging sections with Methods 1 and 3. Therefore, it can be seen that substantially the same $B_1$ non-uniformity reducing effect can be obtained with Methods 1 and 3.

On the basis of the above examination results, it was demonstrated that the $B_1$ non-uniformity reducing effect of the RF shimming can be maximized by the method of this embodiment for all the imaging sections even for a cervical vertebra region showing large change of the AX sectional shape along the z-axis direction.

As explained above, the MRI apparatus 100 of this embodiment is provided with the static magnetic field formation part for forming a static magnetic field, the gradient magnetic field application part for applying a gradient magnetic field, the radio frequency magnetic field transmission part having a plurality of channels for transmitting different radio frequency magnetic fields to a subject, the signal reception part for receiving magnetic resonance signals generated from the subject, the distribution calculation part 331 for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and the condition calculation part 332 for calculating, as a radio frequency magnetic field condition, at least one of phase and amplitude of a radio frequency magnetic field irradiated from each of the plurality of channels among imaging conditions for an arbitrary imaging section as an object of imaging on the basis of the first radio frequency magnetic field distribution.

In the above apparatus, the distribution calculation part 331 may further calculate a second radio frequency magnetic field distribution as a radio frequency magnetic field distribution of a second distribution measurement section perpendicular to the first axis from the magnetic resonance signals, and the condition calculation part 332 may calculate the radio frequency magnetic field condition further on the basis of the second radio frequency magnetic field distribution.

Further, when the imaging section is a section perpendicular to a second axis different from the first axis, the condition calculation part 332 may be provided with a distribution extraction part 334 for extracting a radio frequency magnetic field distribution of a crossing region as a radio frequency magnetic field distribution of a region containing a line of intersection of the imaging section and the first distribution measurement section from the first radio frequency magnetic field distribution, and calculate the radio frequency magnetic field condition of the imaging section by using the radio frequency magnetic field distribution of the crossing region. On the other hand, when the imaging section is a section perpendicular to the first axis and different from both the first distribution measurement section and the second distribution measurement section, the condition calculation part 332 may calculate the radio frequency magnetic field condition of the imaging section by interpolation using a first radio frequency magnetic field condition calculated from the first radio frequency magnetic field distribution and a second radio frequency magnetic field condition calculated from the second radio frequency magnetic field distribution.

As described above, according to this embodiment, $B_1$ distributions of only several sections of a predetermined one direction are measured, and the radio frequency magnetic field condition that maximizes the $B_1$ non-uniformity reducing effect for an imaging section of an arbitrary direction and at arbitrary position is calculated from the $B_1$ distribution data. For example, $B_1$ distributions are measured for only several sections of the AX direction, then the optimal radio frequency magnetic field condition for an imaging section of the AX direction at an arbitrary position is obtained by interpolation from the optimal radio frequency magnetic field conditions calculated from two $B_1$ distributions for sections near the imaging section, and the optimal radio frequency magnetic field condition for an imaging section of the SAG or COR direction at an arbitrary position is obtained by using only $B_1$ values of a crossing region with the imaging section extracted from the $B_1$ distributions.

That is, according to this embodiment, the radio frequency magnetic field conditions for arbitrary imaging sections for every channel are calculated by using $B_1$ distributions of distribution measurement sections of one axis direction. Therefore, time required for the measurement of $B_1$ distribution is short, and therefore extension of the total imaging time is suppressed. Further, the radio frequency magnetic field conditions for imaging sections are calculated for the measurement axis direction and the other directions by a method optimal for each direction utilizing the characteristics of change of the $B_1$ distribution depending on the characteristics of the transmission coil, the shape of the subject, and so forth. Therefore, the optimal radio frequency magnetic field conditions for each imaging section can be obtained with accuracy substantially the same level as that of the optimal radio frequency magnetic field conditions obtained from $B_1$ distribution of the actual imaging section, and equivalent $B_1$ non-uniformity reducing effect can be obtained.

Further, in this embodiment, in particular, one direction is used as the measurement axis. Such one direction of sections for performing the $B_1$ distribution measurement enables use of the multi-slice method for the $B_1$ distribution measurement. Therefore, $B_1$ distributions of all the required distribution measurement sections can be measured with the same measurement time as that for measurement of $B_1$ distribution of one section, and thus the time required for the $B_1$ distribution measurement can be shortened.

As explained above, according to this embodiment, with minimizing extension of the imaging time, the $B_1$ non-uniformity reducing effect of RF shimming can be maximized regardless of the position or direction of the imaging section. Therefore, an image of high image quality can be efficiently obtained regardless of the position or direction of the imaging section.

In the above explanation of this embodiment, the optimal radio frequency magnetic field conditions are calculated from $B_1$ distributions of distribution measurement sections using the aforementioned equation (2). However, the method for calculating the radio frequency magnetic field conditions (amplitude and phase of RF) from $B_1$ distributions of distribution measurement sections is not limited to this method. For example, the method described in Patent document 2 may be used. That is, after amplitude and phase of RF are changed with a certain interval, and uniformity of each is calculated, the phase and amplitude of RF providing the highest uniformity may be used as the phase and amplitude of the optimal RF.

Further, in the above explanation of this embodiment, amplitude and phase of RF optimal for reducing non-uniformity of $B_1$ distribution are calculated as the radio frequency magnetic field conditions. However, it is not necessarily required to calculate both of the amplitude and phase of RF, and either one may be calculated. For example, when it is desired to control only the phase, x can be calculated by solving the equation (2) using a fixed value of the amplitude. Similarly, when it is desired to control only the amplitude, x can be calculated by solving the equation (2) using a fixed value of the phase.

Further, this embodiment was explained above by exemplifying a case where the imaging sections mainly consist of sections of three directions, i.e., AX section, SAG section, and COR section. However, the imaging section is not limited to these. The sections may be sections oblique from these directions by a predetermined angle. That is, the imaging section may be an imaging section of oblique imaging. The condition calculation part 332 makes the distribution extraction part 334 extract $B_1$ values of a crossing region of an imaging section and a distribution measurement section, and calculates the optimal radio frequency magnetic field condition for the imaging section by using them, so long as the imaging section is not parallel to the distribution measurement section.

Figure 14:
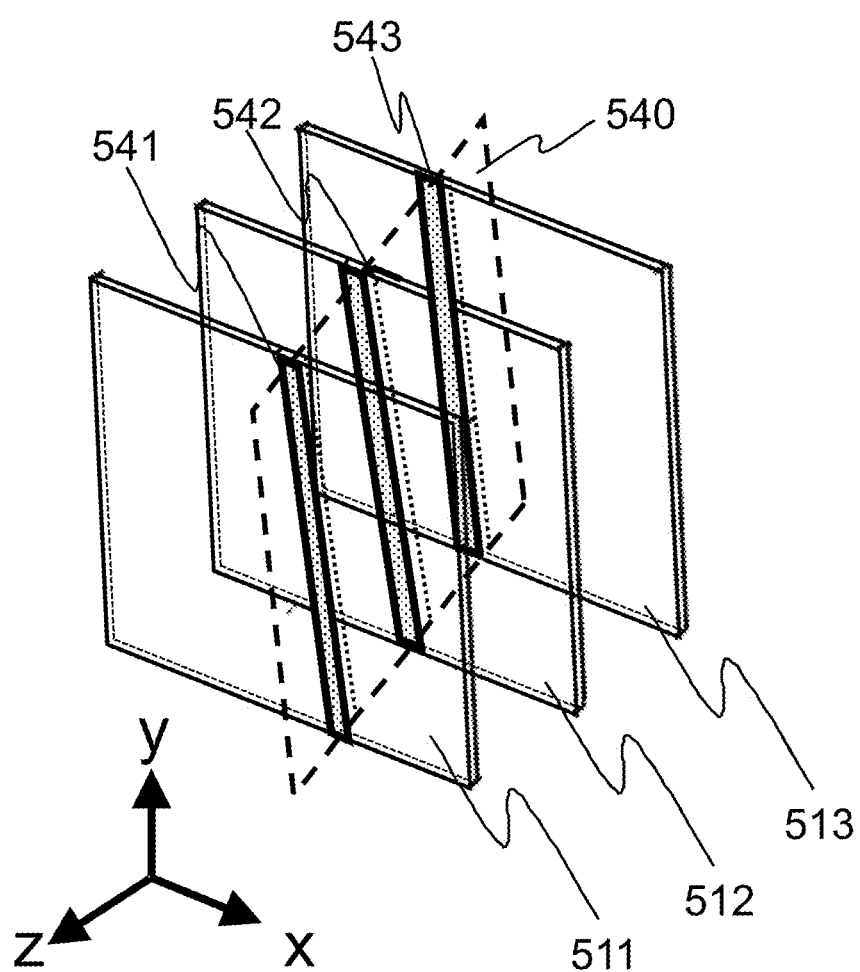
FIG. 14 an explanatory drawing for explaining the method of RF shimming according to the first embodiment for the case where the imaging section is an oblique section.

FIG. 14 is a drawing for explaining a region from which $B_1$ values are extracted (crossing region) for the case of performing oblique imaging for a section oblique from the SAG section by a predetermined angle as an imaging section. The distribution measurement sections consist of three sections 511, 512, and 513 of the AX direction, like the aforementioned embodiment.

As shown in this drawing, also in the case of the oblique imaging, predetermined regions containing lines of intersection of the imaging section 540 and the distribution measurement sections 511, 512, and 513 are considered as crossing regions 541, 542, and 543, and $B_1$ values of the crossing regions are extracted. And the same processing as that for the aforementioned case where the imaging section 540 is perpendicular to an axis other than the measurement axis is performed to calculate the optimal radio frequency magnetic field conditions.

However, in the case of the oblique imaging, as the oblique angle becomes larger, a possibility that the imaging section does not intersect with all the distribution measurement sections becomes higher. Therefore, for the oblique imaging, an appropriate countermeasure is used as required, for example, the number N of the distribution measurement sections is increased, or the intervals between the distribution measurement sections are made smaller.

Further, for example, when there is at least one distribution measurement section not crossing the imaging section 540, an error message may be displayed. Specifically, when $B_1$ distributions of three AX sections as the distribution measurement sections are obtained, and the distribution extraction part 334 extracts $B_1$ distributions of crossing regions with the imaging section for oblique imaging, if there is a distribution measurement section giving an extracted $B_1$ value of zero, an error message is outputted. The apparatus may have such a configuration that a certain countermeasure can then be employed by users, for example, the number of the distribution measurement sections can be increased, or the intervals between the distribution measurement sections can be made smaller. Alternatively, the apparatus may have such a configuration that in response to outputting of the error message by the distribution extraction part 334, the distribution calculation part 331 changes the conditions of the distribution calculation processing, for example, increases the number of the distribution measurement sections by a predetermined number, or makes the intervals between the distribution measurement sections smaller, and the $B_1$ distribution measurement is performed again. By introducing such a flow, optimal RF amplitude and phase can be calculated even when the oblique angle of the imaging section is large.

Further, this embodiment was explained above by exemplifying a case where the number N of the distribution measurement sections is 3 as a specific example. However, the distribution measurement section number N may be 1, for example, when the sectional shape change of the subject 103 is small along the measurement axis direction. In the aforementioned specific example, if the shape change of the AX section of the subject 103 is small, and the shape of the section is substantially the same for the z-axis direction, it corresponds to such a case as mentioned above. This is because if the shape of the AX section of the subject 103 is substantially the same, the $B_1$ distribution is also substantially the same at any position of the section. In such a case, by setting N to be 1 (N=1), it becomes easy to set the position of the distribution measurement section for which the $B_1$ distribution is measured. Further, also when FOV for the measurement axis direction is small, N may be set to be 1 (N=1). If FOV for the z-axis direction is small in the aforementioned example, it corresponds to such a case as mentioned above.

When the number of the distribution measurement section is set to be 1 (N=1), for the imaging section of the measurement axis direction, the optimal radio frequency magnetic field condition for the distribution measurement section is used as the radio frequency magnetic field condition for the imaging section as it is. Further, for the imaging sections of a direction other than the measurement axis direction, radio frequency magnetic field conditions calculated by using the $B_1$ distribution of a crossing region with that distribution measurement section are used as the optimal radio frequency magnetic field conditions.

On the other hand, when it is known beforehand that change of the sectional shape of the subject 103 is large for the measurement axis direction, the number of N is set to be large. That is, if shape change of the AX section of the subject 103 for the z-axis direction is large in the aforementioned specific example, N may be set to be 4 (N=4) or larger.

Further, the number of the distribution measurement sections may be determined depending on change of the sectional shape of the subject for the measurement axis direction, size of FOV, and so forth.

Further, as explained in the explanation of the aforementioned embodiment, the measurement axis direction of the distribution measurement section for which the $B_1$ distribution is measured is desirably a direction for which change of the $B_1$ distribution is small and/or a direction for which shape change of the subject is small, in principle. Therefore, this embodiment was explained above by exemplifying a case where the AX direction satisfying these conditions was the measurement axis direction, as an example. However, the measurement axis direction may not necessarily satisfy these conditions. For example, the measurement axis direction may be the SAG direction or the COR direction.

For example, a case where the importance of sections of a direction other than the direction satisfying the aforementioned conditions is higher than the importance of sections of the direction satisfying the aforementioned conditions in the image acquisition, or a case where imaging is not performed for sections of that direction corresponds to such a case as mentioned above. In such a case, by defining the measurement axis to be the direction of the imaging sections of high importance, $B_1$ non-uniformity reducing effect can be more surely obtained for the imaging sections of high importance.

For example, when the importance of the AX section is low, and the importance of the SAG and COR sections is high in the aforementioned example, or imaging of the AX section is not performed, $B_1$ non-uniformity reducing effect can be more surely obtained for the SAG and COR sections by obtaining the $B_1$ distribution in distribution measurement sections of which measurement axis direction is the SAG direction or the COR direction.

For example, in imaging of cervical vertebra or imaging of lumbar vertebrae, importance of SAG section images may be high. In such a case, SAG sections may be used as the distribution measurement sections, and $B_1$ distributions thereof may be obtained to calculate optimal RF amplitude and phase.

Further, in the explanation of the aforementioned embodiment, the measurement axis is defined to be in one direction. However, it may be in two directions. That is, the distribution measurement sections for which the $B_1$ distribution is measured may be of two directions. For example, if $B_1$ distributions are obtained for the AX direction and the SAG direction, the amount of information concerning the $B_1$ distribution increases. Therefore, higher $B_1$ non-uniformity reducing effect can be realized compared with the case where the optimal radio frequency magnetic field conditions are calculated form $B_1$ distributions for one direction.

Further, the width of the crossing region for direction perpendicular to the imaging section extracted by the distribution extraction part 334 may be optimized by changing the set value of the width as a parameter. In this optimization, a width giving the radio frequency magnetic field condition providing the highest $B_1$ non-uniformity reducing effect is defined to be the optimal value. This is because, if the width of the crossing region is too small, the number of the $B_1$ values to be extracted decreases, and becomes insufficient for calculating amplitude and phase of the optimal RF, but to the contrary, if the length of the crossing region is too large, the positional information is degraded.

Further, in the explanation of the aforementioned embodiment, the optimal radio frequency magnetic field conditions are obtained and set for every imaging section. However, the radio frequency magnetic field conditions may not be obtained for every imaging section. One optimal radio frequency magnetic field condition may be calculated and set for every region having a predetermined width for each axis direction.

Figure 15:
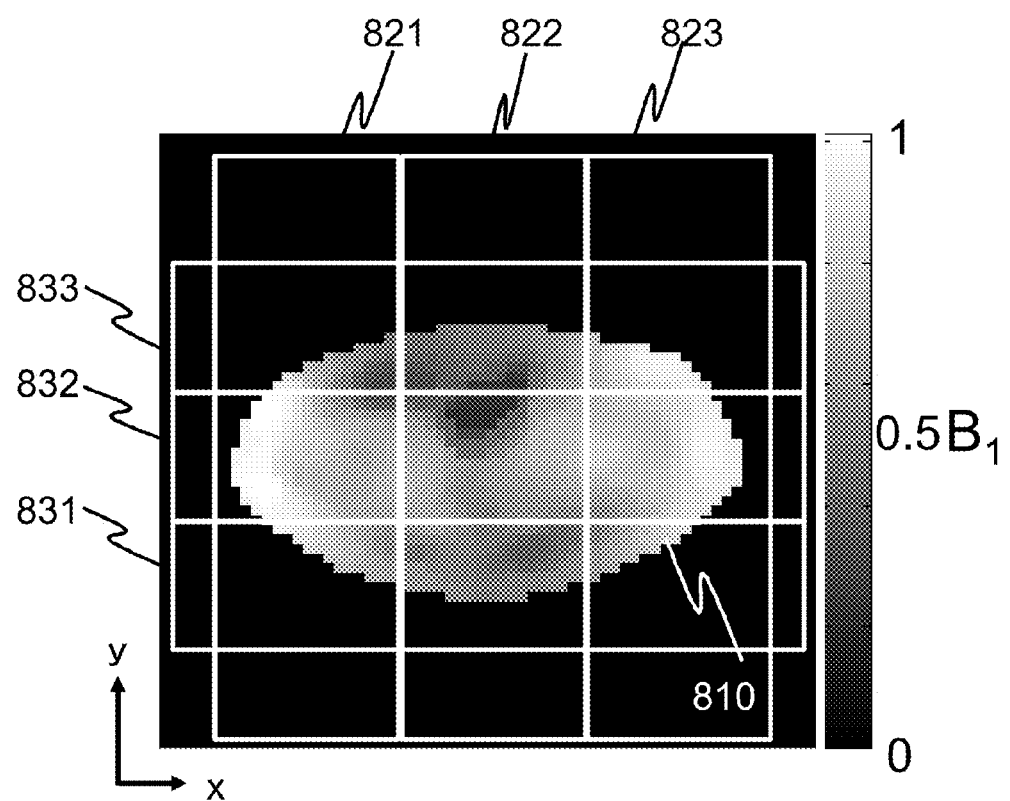
FIG. 15 is an explanatory drawing for explaining a modified example of the first embodiment, which shows regions of the SAG and COR directions on an AX image of a pelvis region.

The case of calculating and setting one optimal radio frequency magnetic field condition for every predetermined region will be explained with reference to a specific example. FIG. 15 shows an AX section 810 of a human pelvis region, regions 821, 822, and 823 obtained by dividing the section into three for the x-axis direction, and regions 831, 832, and 833 obtained by dividing the section into three for the y-axis direction. For the x-axis direction, the whole imaging region is divided into three regions, the region 821 on the left side of the drawing, the 822 at the center, and the region 823 on the right side. Further, for the y-axis direction, the whole imaging region is divided into three regions, the region 831 on the upper side of the drawing, the region 832 at the center, and the region 833 on the lower side.

The distribution extraction part 334 extracts $B_1$ values, for example, for each of the region 821 on the left side, the 822 at the center, and the region 823 on the right side for the x-axis direction. And the condition calculation part 332 calculates the optimal radio frequency magnetic field conditions for each region. That is, amplitude and phase of RF of each channel (A1_L, A2_L, Φ1_L, Φ2_L) are calculated by using the $B_1$ values of the region 821 on the left side, amplitude and phase of RF of each channel (A1_C, A2_C, Φ1_C, Φ2_C) are calculated by using the $B_1$ values of the center region 822, and amplitude and phase of RF of each channel (A1_R, A2_R, Φ1_R, Φ2_R) are calculated by using the $B_1$ values of the region 823 on the right side.

For example, the length for the x-axis direction of the region 822 of a strip shape at the center among the regions divided along the x-axis direction is set to be 150 mm (the position thereof is set to be a position where x is in the range of −75 mm to 75 mm (x=−75 mm to 75 mm), and amplitude and phase of optimal RF (A1_C, A2_C, Φ1_C, Φ2_C) are calculated. For all the imaging sections as the SAG sections of which x-coordinate value is in the range of −75 mm to 75 mm, the amplitude and phase of optimal RF (A1_C, A2_C, Φ1_C, Φ2_C) of the center region 822 are used.

That is, in the above example, the condition calculation part 332 calculates the radio frequency magnetic field conditions for the divided regions obtained by dividing an imaging region including the whole imaging section into a predetermined number of regions along the same direction as that of the imaging section on the basis of the first radio frequency magnetic field distribution, and defines the radio frequency magnetic field condition for the divided region including the imaging section among the divided regions to be the radio frequency magnetic field condition for the imaging section.

As described above, if the optimal radio frequency magnetic field conditions are calculated for a unit of region having a predetermined width, the time and effort required for setting the parameter values of each RF pulse in the sequencer 104 can be reduced compared with the case where one optimal radio frequency magnetic field condition is calculated and set for every imaging section.

Second Embodiment

Hereafter, the second embodiment of the present invention will be explained. According to the first embodiment, the optimal radio frequency magnetic field conditions are set for every imaging section so that the $B_1$ non-uniformity reducing effect is maximized for the corresponding imaging section. In contrast, in this embodiment, the optimal radio frequency magnetic field conditions are set in consideration of the $B_1$ non-uniformity reducing effect for the whole imaging region.

The MRI apparatus according to this embodiment has basically the same configuration as that of the first embodiment. However, as described above, in setting of the optimal radio frequency magnetic field conditions according to this embodiment, the $B_1$ non-uniformity reducing effect for the whole imaging region is taken into consideration. Therefore, the functional configuration of the computer 109 that realizes this characteristic differs from that of the first embodiment. Hereafter, this embodiment will be explained mainly for configurations different from those of the first embodiment.

Figure 16:
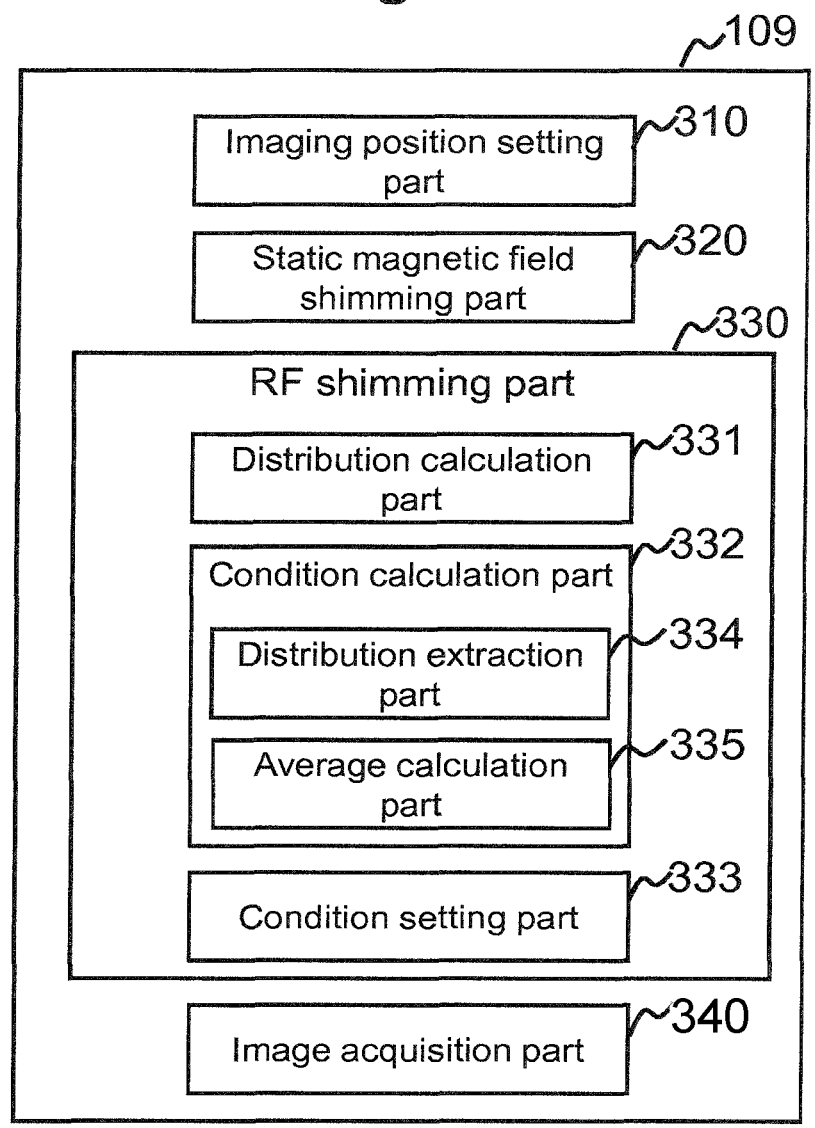
FIG. 16 is a functional block diagram of a computer according to the second embodiment.

FIG. 16 is a functional block diagram of the computer 109 according to this embodiment. As in the first embodiment, the computer 109 according to this embodiment is provided with the imaging position setting part 310, the static magnetic field shimming part 320, the RF shimming part 330, and the image acquisition part 340. The functions of the computer 109 are realized by CPU provided in the computer by loading programs stored in the storage device 111 beforehand on a memory and executing them.

As in the first embodiment, the RF shimming part 330 according to this embodiment is provided with the distribution calculation part 331 for calculating $B_1$ distribution (radio frequency magnetic field distribution) of a distribution measurement section perpendicular to a distribution measurement axis defined beforehand from the magnetic resonance signals, the condition calculation part 332 for calculating the radio frequency magnetic field condition for an arbitrary imaging section by using the obtained $B_1$ distribution, and the condition setting part 333 for setting the obtained radio frequency magnetic field condition as an imaging condition used for the image acquisition. Further, the condition calculation part 332 is provided with the distribution extraction part 334 for extracting $B_1$ distribution ($B_1$ values) of a region containing a line of intersection of the imaging section and the distribution measurement section (henceforth referred to as crossing region) from the $B_1$ distribution of the distribution measurement section. The functions of these parts are basically the same as the functions of the parts having the same names explained for the first embodiment.

However, the condition calculation part 332 according to this embodiment is further provided with an average calculation part 335 for calculating average of $B_1$ values ($B_1$ average) in each distribution measurement section. When the condition calculation part 332 according to this embodiment calculates the optimal radio frequency magnetic field conditions for each distribution measurement section, it takes the $B_1$ average in each distribution measurement section calculated by the average calculation part 335 into consideration. When the imaging section is a section of the measurement axis direction, the condition calculation part 332 of this embodiment adjusts the calculated optimal radio frequency magnetic field conditions for each distribution measurement section so that the $B_1$ averages have similar values, and when the imaging section is not a section of the measurement axis direction, it performs such adjustment that the $B_1$ averages of the extracted $B_1$ distributions of the crossing regions have similar values, and then calculates the optimal radio frequency magnetic field conditions.

For example, when the distribution measurement sections consist of three sections of the AX direction (for example, the sections 511, 512 and 513 shown in FIGS. 8A, 8B, and 8C, which are henceforth referred to as D1, D2, and D3 in this embodiment) ($B_1$ distributions are obtained for the three sections of the AX direction), the condition calculation part 332 calculates the optimal radio frequency magnetic field condition for an imaging section of the measurement axis direction, i.e., an imaging section parallel to the distribution measurement sections (AX section, for example, the section 510 shown in FIG. 8A) by the following method.

First, the condition calculation part 332 calculates the optimal radio frequency magnetic field conditions for the distribution measurement sections (D1, D2, D3) by the same method as that of the first embodiment. Further, it makes the average calculation part 335 calculate $B_1$ averages for the distribution measurement sections (D1, D2, D3), and register them at, for example, the storage device 111. For the following explanation, it is supposed that the obtained $B_1$ averages for the distribution measurement sections (D1, D2, D3) are 0.8, 1.0, and 0.8, respectively.

Then, the condition calculation part 332 adjusts the $B_1$ averages for the distribution measurement sections (D1, D2, D3) so that the $B_1$ averages for all the distribution measurement sections have the same values, and registers them at the storage device 111. In this example, for example, the optimal radio frequency magnetic field conditions for the distribution measurement sections D1 and D3 are multiplied with 1.25, so that the $B_1$ averages for all the distribution measurement sections have a value of 1.0. And the optimal radio frequency magnetic field conditions for the imaging sections are calculated by interpolation or the like by the same method as that used in the first embodiment using the adjusted optimal radio frequency magnetic field conditions for the distribution measurement sections.

Further, when the distribution measurement sections consist of D1, D2, and D3 mentioned above, the condition calculation part 332 calculates the optimal radio frequency magnetic field condition for an imaging section other than those of the measurement axis direction, i.e., an imaging section not parallel to the distribution measurement section, such as an SAG section (for example, the section 520 shown in FIG. 8B) and a COR section (for example, the section 530 shown in FIG. 8C) by the following method.

The condition calculation part 332 first makes the distribution extraction part 334 extract $B_1$ values of the crossing regions of an imaging section and the distribution measurement sections (D1, D2, D3) by the same method as that used in the first embodiment. For example, it is supposed that images of two SAG sections (for example, the section 520 shown in FIG. 8B) are obtained. The crossing regions of the first imaging section and the distribution measurement sections (for example, the regions 521, 522 and 523 shown in FIG. 8B) are henceforth referred to as E1_1, E1_2, and E1_3 in this embodiment, and the crossing regions of the second imaging section and the distribution measurement sections (for example, the regions 521, 522 and 523 shown in FIG. 8B) are henceforth referred to as E2_1, E2_2, and E2_3 in this embodiment. And the average calculation part 335 is made to calculate $B_1$ averages of all the crossing regions E1_1, E1_2, and E1_3, and $B_1$ averages of all the crossing regions E2_1, E2_2, and E2_3. And the condition calculation part 332 calculates the optimal radio frequency magnetic field conditions for the imaging sections so that the $B_1$ averages for all the imaging section positions (positions of the two sections in this case) have the same value by the method used in the first embodiment.

For example, if it is supposed that the $B_1$ averages for two imaging section positions are 0.8 and 1.0 in the aforementioned example, the condition calculation part 332 multiplies the optimal radio frequency magnetic field condition for the imaging section of which $B_1$ average is 0.8 with 1.25 so that, for example, all the $B_1$ averages for the distribution measurement sections have a value of 1.0.

This embodiment is applied to a case where the number of the distribution measurement sections is 2 or larger.

Figure 17:
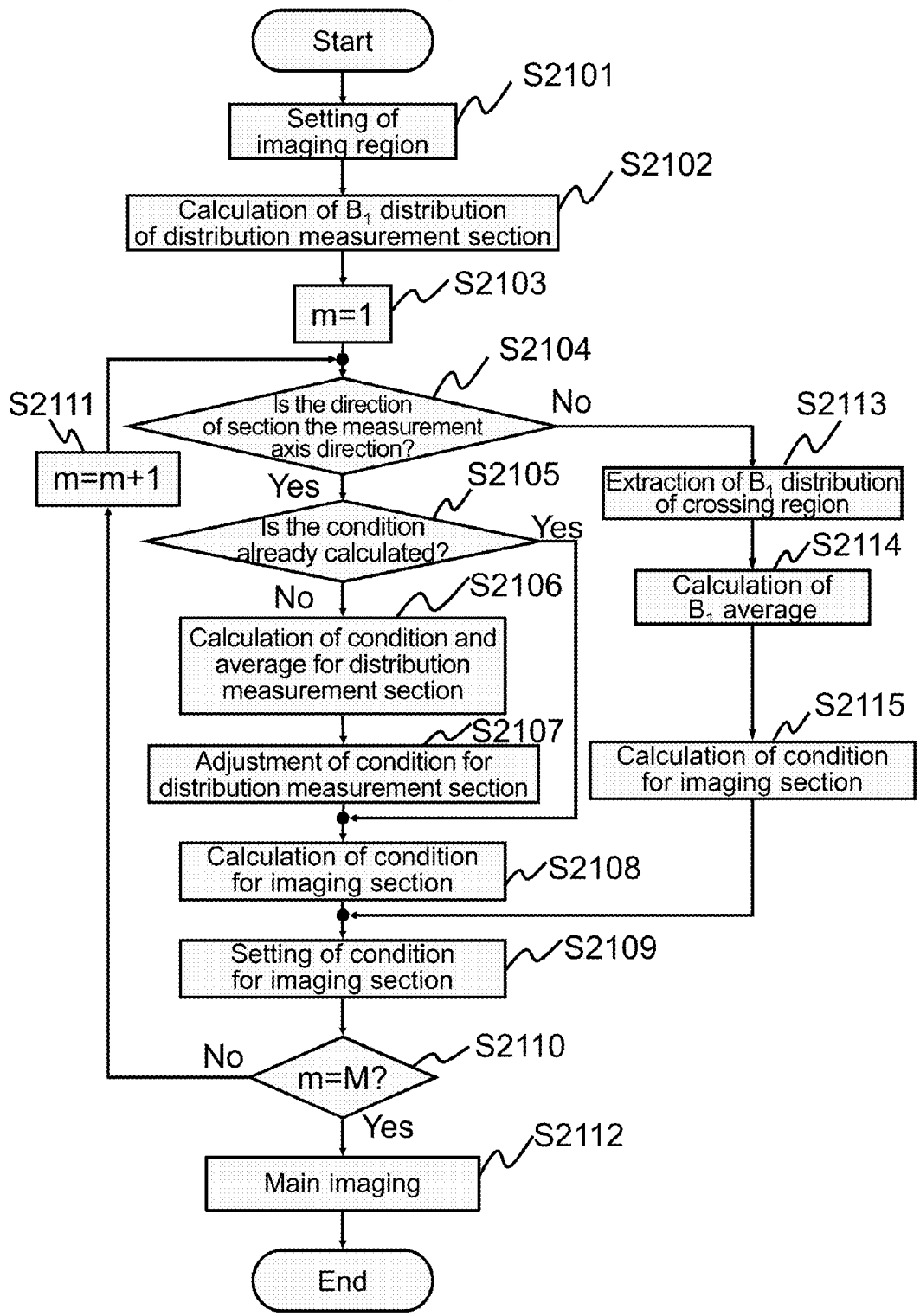
FIG. 17 is a flowchart of the imaging processing according to the second embodiment.

Hereafter, the flow of the imaging processing performed by the computer 109 according to this embodiment will be explained with reference to FIG. 17. FIG. 17 shows the process flow of the imaging processing according to this embodiment. In this case, the measurement axis direction is defined to be the AX direction, and the number of the distribution measurement sections is defined to be N(N is an integer of 2 or larger). Further, the number of the imaging sections is defined to be M (M is an integer of 1 or larger).

First, the imaging position setting part 310 performs imaging region setting processing (Step S2101). Then, the distribution calculation part 331 performs $B_1$ distribution measurement, and calculates $B_1$ distributions of N of the distribution measurement sections along the AX direction (Step S2102). In this calculation, the distribution calculation part 331 determines the imaging regions for which $B_1$ distribution is measured with reference to parameters concerning the position of the image obtaining in the image acquisition calculated by the imaging position setting part 310.

Then, the RF shimming part 330 performs the RF shimming processing for every imaging section set by the imaging position setting part 310. In this processing, the condition calculation part 332 calculates the optimal radio frequency magnetic field conditions for every imaging section, and the condition setting part 333 sets the calculated radio frequency magnetic field conditions.

As the RF shimming processing, the RF shimming part 330 repeats the following processings a number of times corresponding to the total number of imaging sections, i.e., M times (Steps S2103, S2110, and S2111).

First, the condition calculation part 332 determines whether the direction of the m-th imaging section (m is an integer satisfying 1≤m≤M) as the object of the processing is the measurement axis direction or not (Step S2104). And if it is the measurement axis direction, the condition calculation part 332 determines whether the adjusted optimal radio frequency magnetic field conditions for the distribution measurement sections are already calculated or not (Step S2105). Whether they are already calculated or not is determined on the basis of, for example, whether the adjusted optimal radio frequency magnetic field conditions for the distribution measurement sections are registered at the storage device 111 or not.

When it is determined that they are not calculated yet in Step S2105, the condition calculation part 332 first calculates the optimal radio frequency magnetic field conditions and $B_1$ averages for the distribution measurement sections (Step S2106).

As described above, the average calculation part 321 is made to calculate the $B_1$ averages. And the condition calculation part 332 adjusts the optimal radio frequency magnetic field conditions for the distribution measurement sections by the aforementioned method using the calculated $B_1$ averages, registers them at the storage device 111 as the adjusted radio frequency magnetic field conditions (Step S2107), and calculates the optimal radio frequency magnetic field condition for the m-th imaging section according to the aforementioned method by using the obtained adjusted optimal radio frequency magnetic field conditions for the distribution measurement sections (Step S2108). On the other hand, when it is determined that they are already calculated in Step S2105, the process moves to Step S2108, and the optimal radio frequency magnetic field condition for the m-th imaging section is calculated according to the aforementioned method by using the already calculated optimal radio frequency magnetic field conditions for the distribution measurement sections.

The condition setting part 333 sets the calculated optimal radio frequency magnetic field condition as the imaging condition for the m-th imaging section (Step S2109). And the condition setting part 333 determines whether the processing is finished for all the imaging sections or not (Step S2110), and if it is not finished, m is incremented by one (Step S2111), the process returns to Step S2103, and the processing is repeated.

When it is determined that the processing is finished for all the imaging sections in Step S2110, the RF shimming part 330 finishes the RF shimming processing, and the image acquisition part 340 performs the image acquisition (Step S2112).

On the other hand, when it is determined that the m-th imaging section as the object of the processing is not a section of the measurement axis direction in Step S2104, the condition calculation part 332 makes the distribution extraction part 334 extract $B_1$ distributions of the crossing regions of the m-th imaging section and the distribution measurement sections (Step S2113). And the condition calculation part 332 makes the average calculation part 335 calculate averages of the $B_1$ distributions ($B_1$ values) for the crossing regions (Step S2114). And the condition calculation part 332 calculates the optimal radio frequency magnetic field condition for the m-th imaging section according to the aforementioned method (Step S2115). And the process moves to Step S2109.

In the above, the flow of the whole imaging processing including the RF shimming according to this embodiment was explained.

As explained above, the MRI apparatus 100 of this embodiment is provided with the static magnetic field formation part for forming a static magnetic field, the gradient magnetic field application part for applying a gradient magnetic field, the radio frequency magnetic field transmission part having a plurality of channels for transmitting different radio frequency magnetic fields to a subject, the signal reception part for receiving magnetic resonance signals generated from the subject, the distribution calculation part 331 for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and the condition calculation part 332 for calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution.

Further, when the first distribution measurement section consists of a plurality of sections, and the imaging section is a section perpendicular to the first axis and different from any of the plurality of the first distribution measurement sections, the condition calculation part 332 is further provided with the average calculation part 335 for calculating a magnetic field average as an average of radio frequency magnetic field values in each first distribution measurement section for each of the plurality of the first distribution measurement sections, adjusts the radio frequency magnetic field conditions for the first measurement sections so that the magnetic field averages have the same value, and performs interpolation with the adjusted radio frequency magnetic field conditions to calculate the radio frequency magnetic field condition for the imaging section.

When the first distribution measurement section consists of a plurality of sections, and the imaging section is a section perpendicular to a second axis different from the first axis, the condition calculation part 332 is provided with the distribution extraction part 334 for extracting crossing region radio frequency magnetic field distributions as radio frequency magnetic field distributions of regions containing lines of intersection of the first distribution measurement sections and the imaging section from the first radio frequency magnetic field distributions, and the average calculation part 335 for calculating magnetic field averages as averages of radio frequency magnetic field values in the regions containing the lines of intersection for every region, and calculates the radio frequency magnetic field condition for the imaging section so that the magnetic field averages have the same values.

That is, according to this embodiment, the optimal radio frequency magnetic field conditions for the imaging sections are calculated by using $B_1$ distributions of the distribution measurement sections of one axis direction and utilizing the characteristics of change of the $B_1$ distribution according to an optimal method for every imaging section, as in the first embodiment. Further, the measurement axis direction is limited to one direction. Therefore, like the first embodiment, the optimal radio frequency magnetic field condition for each imaging section can be obtained with accuracy substantially the same level as that of the optimal radio frequency magnetic field conditions obtained from actual $B_1$ distribution of the imaging section, and equivalent $B_1$ non-uniformity reducing effect can be obtained.

Therefore, like the first embodiment, with minimizing extension of the imaging time, the $B_1$ non-uniformity reducing effect of RF shimming can be maximized regardless of the position and the direction of the imaging section, and an image of high image quality can be efficiently obtained regardless of the position and the direction of the imaging section.

Furthermore, since such an adjustment that the $B_1$ averages for a plurality of the distribution measurement sections have similar value is performed in this embodiment, the $B_1$ non-uniformity reducing effect can be further enhanced, and an image of further higher quality can be obtained.

In addition, also in this embodiment, other methods may be used for the method for calculating $B_1$ distribution, like the first embodiment. Further, the optimal radio frequency magnetic field condition may be either one of amplitude and phase of RF. Further, the direction of the imaging section may be an oblique direction. In such a case, the same countermeasures as those mentioned for the first embodiment may be used. Further, the number of distribution measurement sections may be determined according to change of the sectional shape of the subject for the measurement axis direction, the size of FOV, and so forth. Further, as the measurement axis direction, a desired direction may be chosen according to the imaging conditions and the imaging object. Further, the measurement axis direction may be set in two directions. Further, also in this embodiment, the optimal radio frequency magnetic field conditions may be set in a unit of region, like the first embodiment.

Third Embodiment

Hereafter, the third embodiment of the present invention will be explained. According to this embodiment, amplitude and phase of RF are determined as the optimal radio frequency magnetic field conditions under a restriction that the radio frequency magnetic field (RF) output does not exceed an upper limit thereof.

The upper limit of RF output is determined according to, for example, the upper limit of the amount of energy of RF absorbed by a human body (specific absorption ratio, SAR), the maximum output value of RF amplifier, or the like. Further, there are two kinds of SAR, i.e., whole body SAR representing energy absorbed by the whole human body, and local SAR representing energy locally absorbed in a human body. According to this embodiment, the upper limit of RF output is determined so that the whole body SAR or local SAR is suppressed so as not to affect the human body. The upper limit of RF output is determined on the basis of, for example, correlation of RF output, magnetic field ($B_1$ value) and SAR value obtained by electromagnetic field analysis simulation.

The MRI apparatus 100 according to this embodiment has basically the same configuration as that of the first embodiment. However, as described above, in setting of the optimal radio frequency magnetic field conditions according to this embodiment, the upper limit of RF output is taken into consideration. Therefore, the functional configuration of the computer 109 that realizes this characteristic differs from that of the first embodiment. Hereafter, this embodiment will be explained mainly for configurations different from those of the first embodiment.

Figure 18:
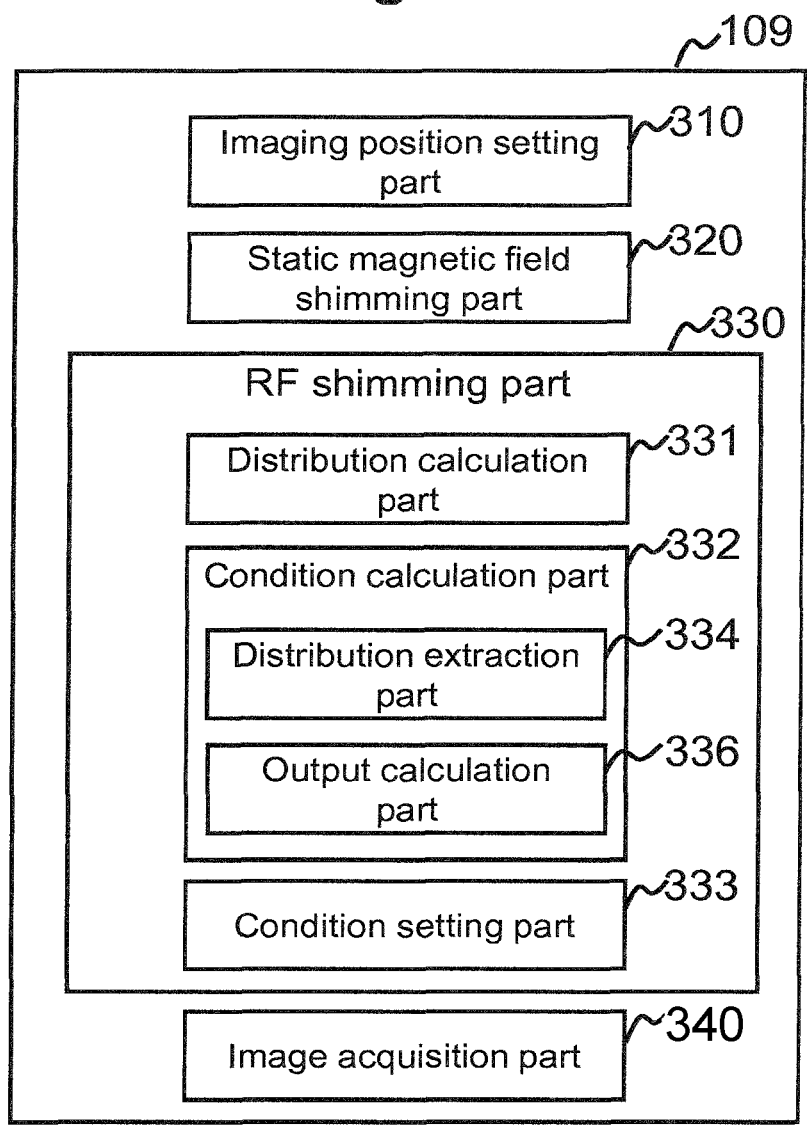
FIG. 18 is a functional block diagram of a computer according to the third embodiment.

FIG. 18 is a functional block diagram of the computer 109 according to this embodiment. As shown in this drawing, as in the first embodiment, the computer 109 according to this embodiment is provided with the imaging position setting part 310, the static magnetic field shimming part 320, the RF shimming part 330, and the image acquisition part 340. The functions of the computer 109 are realized by CPU provided in the computer by loading programs stored in the storage device 111 beforehand on a memory and executing them.

Further, as in the first embodiment, the RF shimming part 330 according to this embodiment is provided with the distribution calculation part 331 for calculating $B_1$ distribution (radio frequency magnetic field distribution) of a distribution measurement section perpendicular to a distribution measurement axis defined beforehand from the magnetic resonance signals, the condition calculation part 332 for calculating the radio frequency magnetic field condition for an arbitrary imaging section by using the obtained $B_1$ distribution, and the condition setting part 333 for setting the obtained radio frequency magnetic field condition as an imaging condition used for the image acquisition. Further, the condition calculation part 332 is provided with the distribution extraction part 334 for extracting $B_1$ distribution ($B_1$ values) of a region containing a line of intersection of the imaging section and the distribution measurement section (henceforth referred to as crossing region) from the $B_1$ distribution of the distribution measurement section. The functions of these parts are basically the same as the functions of the parts having the same names explained for the first embodiment.

However, the condition calculation part 332 according to this embodiment is further provided with an output calculation part 336 for calculating a ratio of SAR observed at the time of transmitting RF under the calculated optimal radio frequency magnetic field condition to a predetermined upper limit of SAR. According to this embodiment, for example, the RF output and the value of SAR are correlated beforehand by electromagnetic field analysis simulation, and a value of SAR corresponding to a certain RF output is obtained from that correlation. Further, the upper limit of SAR is determined from the value of SAR determined in consideration of the safety to human bodies, or the like. The output calculation part 336 divides the value of SAR with the SAR upper limit to calculate the aforementioned ratio.

When the imaging section is a section of the measurement axis direction, and the ratio calculated by the output calculation part 336 exceeds 1, the condition calculation part 332 adjusts the amplitude of RF of the optimal radio frequency magnetic field condition for the concerned distribution measurement section by dividing it with the obtained ratio so that it does not exceed the SAR upper limit.

For example, when the distribution measurement sections consist of three sections of the AX direction (for example, the sections 511, 512 and 513 shown in FIGS. 8A, 8B, and 8C, which are henceforth referred to as D1, D2, and D3 in this embodiment) ($B_1$ distributions are obtained for the three sections of the AX direction), the condition calculation part 332 calculates the optimal radio frequency magnetic field condition for an imaging section of the measurement axis direction, i.e., an imaging section parallel to the distribution measurement sections (AX section, for example, the section 510 shown in FIG. 8A) by the following method.

First, the condition calculation part 332 calculates the optimal radio frequency magnetic field conditions for the distribution measurement sections (D1, D2, D3) by the same method as that of the first embodiment. The output calculation part 336 calculates the ratios using the values of SAR of the distribution measurement sections (D1, D2, D3) and the SAR upper limit. And for any distribution measurement section giving a value of the ratio exceeding 1, the condition calculation part 332 divides the calculated optimal radio frequency magnetic field condition with the ratio to obtain an adjusted optimal radio frequency magnetic field condition.

For example, when the obtained ratios of the distribution measurement sections (D1, D2, D3) are 1.25, 1, and 1, the condition calculation part 332 divides the amplitude of RF as the optimal radio frequency magnetic field condition of the distribution measurement section D1 with 1.25, namely, multiplies it with 0.8, to obtain the adjusted optimal radio frequency magnetic field condition. Then, the optimal radio frequency magnetic field condition for the imaging section are calculated by interpolation or the like by the same method as that used in the first embodiment using the adjusted optimal radio frequency magnetic field conditions for the distribution measurement sections.

Further, when the distribution measurement sections consist of D1, D2, and D3 mentioned above, the condition calculation part 332 calculates the optimal radio frequency magnetic field condition for an imaging section other than that of the measurement axis direction, i.e., an imaging section not parallel to the distribution measurement section, such as an SAG section (for example, the section 520 shown in FIG. 8B) and a COR section (for example, the section 530 shown in FIG. 8C) by the following method.

The condition calculation part 332 first makes the distribution extraction part 334 extract $B_1$ values of the crossing regions of an imaging section and the distribution measurement sections (D1, D2, D3) by the same method as that used in the first embodiment. For example, it is supposed that images of two SAG sections (for example, the section 520 shown in FIG. 8B) are obtained. The crossing regions of the first imaging section and the distribution measurement sections (for example, the regions 521, 522 and 523 shown in FIG. 8B) are henceforth referred to as E1_1, E1_2, and E1_3 in this embodiment, and the crossing regions of the second imaging section and the distribution measurement sections (for example, the regions 521, 522 and 523 shown in FIG. 8B) are henceforth referred to as E2_1, E2_2, and E2_3 in this embodiment. The output calculation part 336 calculates the ratios using the values of SAR of the distribution measurement sections and the upper limit of SAR. Then, the optimal radio frequency magnetic field conditions are calculated by using the adjusted $B_1$ values of the crossing regions.

For example, when the ratios for the two imaging section positions are 1.25 and 1, the condition calculation part 332 divides the optimal radio frequency magnetic field condition for the imaging section of the ratio of 1.25 with 1.25, i.e., multiplies it with 0.8. Then, the optimal radio frequency magnetic field conditions for the imaging sections are calculated.

Whether the ratio exceeds the upper limit of SAR is determined for, for example, all the distribution measurement sections or all the crossing regions. This is because even when imaging is performed for a predetermined imaging section, RF is irradiated to the whole of the subject 103.

Hereafter, the flow of the imaging processing performed by the computer 109 according to this embodiment will be explained with reference to FIG. 19. FIG. 19 shows the process flow of the imaging processing according to this embodiment. In this case, the measurement axis direction is defined to be the AX direction, and the number of the distribution measurement sections is defined to be N(N is an integer of 2 or larger). Further, the number of the imaging sections is defined to be M (M is an integer of 1 or larger).

First, the imaging position setting part 310 performs imaging region setting processing (Step S3101). Then, the distribution calculation part 331 performs $B_1$ distribution measurement, and calculates $B_1$ distributions of N of the distribution measurement sections along the AX direction (Step S3102). In this calculation, the distribution calculation part 331 determines the imaging regions for which $B_1$ distribution is measured with reference to parameters concerning the position of the image obtaining in the image acquisition calculated by the imaging position setting part 310.

Then, the RF shimming part 330 performs the RF shimming processing for every imaging section set by the imaging position setting part 310. In this processing, the condition calculation part 332 calculates the optimal radio frequency magnetic field condition for every imaging section, and sets the radio frequency magnetic field conditions calculated by the condition setting part 333.

As the RF shimming processing, the RF shimming part 330 repeats the following processings a number of times corresponding to the total number of the imaging sections, i.e., M times (Steps S3103, S3111, and S3112).

First, the condition calculation part 332 determines whether the direction of the m-th imaging section (m is an integer satisfying 1≤m≤M) of the object of the processing is the measurement axis direction or not (Step S3104). And if it is the measurement axis direction, the condition calculation part 332 determines whether the optimal radio frequency magnetic field conditions for the distribution measurement sections are already calculated or not (Step S3105). Whether they are already calculated or not is determined on the basis of, for example, whether the adjusted optimal radio frequency magnetic field conditions for the distribution measurement sections are registered at the storage device 111 or not.

When it is determined that they are not calculated yet in Step S3105, the condition calculation part 332 first calculates the optimal radio frequency magnetic field conditions for the distribution measurement sections (Step S3106). And the condition calculation part 332 calculates the ratios by using the values of SAR of the distribution measurement sections and the upper limit of SAR (Step S3107). The calculation is performed by the output calculation part 336 as described above.

Then, the condition calculation part 332 adjusts the optimal radio frequency magnetic field conditions for the distribution measurement sections by the aforementioned method according to the obtained ratios, registers them at the storage device 111 as the adjusted radio frequency magnetic field conditions (Step S3108), and calculates the optimal radio frequency magnetic field condition for the m-th imaging section according to the aforementioned method by using the obtained adjusted optimal radio frequency magnetic field conditions for the distribution measurement sections (Step S3109). On the other hand, when it is determined that they are already calculated in Step S3105, the process moves to Step S3109, and the optimal radio frequency magnetic field condition for the m-th imaging section is calculated according to the aforementioned method by using the already calculated optimal radio frequency magnetic field conditions for the distribution measurement sections.

The condition setting part 333 sets the calculated optimal radio frequency magnetic field condition as the imaging condition for the m-th imaging section (Step S3110). And the condition setting part 333 determines whether the processing is finished for all the imaging sections or not (Step S3111), and if it is not finished, m is incremented by one (Step S3112), the process returns to Step S3104, and the processing is repeated.

When it is determined that the processing is finished for all the imaging sections in Step S3111, the RF shimming part 330 finishes the RF shimming processing, and the image acquisition part 340 performs the image acquisition (Step S3113).

On the other hand, when it is determined that the m-th imaging section of the object of the processing is not a section of the measurement axis direction in Step S3104, the condition calculation part 332 makes the distribution extraction part 334 extract $B_1$ distributions of the crossing regions of the m-th imaging section and the distribution measurement sections (Step S3114). Then, the condition calculation part 332 makes the output calculation part 336 calculate the ratios of SAR according to the aforementioned method (Step S3115), and calculates the optimal radio frequency magnetic field condition for the m-th imaging section (Step S3116). And the process moves to Step S3110.

In the above, the flow of the whole imaging processing including the RF shimming according to this embodiment was explained.

As explained above, the MRI apparatus 100 according to this embodiment is provided with the static magnetic field formation part for forming a static magnetic field, the gradient magnetic field application part for applying a gradient magnetic field, the radio frequency magnetic field transmission part having a plurality of channels for transmitting different radio frequency magnetic fields to a subject, the signal reception part for receiving magnetic resonance signals generated from the subject, the distribution calculation part 331 for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and the condition calculation part 332 for calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution.

Further, the condition calculation part 332 is provided with the output calculation part 336 for calculating a ratio of SAR observed at the time of irradiating the radio frequency magnetic field from the radio frequency magnetic field irradiation part under the calculated radio frequency magnetic field condition to a predetermined upper limit of SAR by using either one of the first radio frequency magnetic field distribution and the calculated radio frequency magnetic field condition, and when the result of the calculation performed by the output calculation part 336 exceeds 1, adjusts the radio frequency magnetic field condition so that the calculation result become 1 or smaller.

That is, according to this embodiment, the optimal radio frequency magnetic field condition for the imaging section is calculated by using $B_1$ distributions of the distribution measurement sections of one axis direction and utilizing the characteristics of change of the $B_1$ distribution according to an optimal method for every imaging section, as in the first embodiment. Further, the measurement axis direction is limited to one direction. Therefore, like the first embodiment, the optimal radio frequency magnetic field conditions for the imaging sections can be obtained with accuracy substantially the same as that of the optimal radio frequency magnetic field conditions obtained from actual $B_1$ distributions of the imaging sections, and equivalent $B_1$ non-uniformity reducing effect can be obtained.

Therefore, like the first embodiment, with minimizing extension of the imaging time, the $B_1$ non-uniformity reducing effect of RF shimming can be maximized regardless of the position and the direction of the imaging section, and an image of high image quality can be efficiently obtained regardless of the position and the direction of the imaging section.

Furthermore, according to this embodiment, an adjustment is performed so that the output of RF does not exceed a predetermined upper limit of SAR. Therefore, a highly safe MRI apparatus can be provided.

In the aforementioned explanation of this embodiment, the values of SAR and the upper limit of SAR are determined on the basis of electromagnetic field analysis simulation data, but the determination method for these values is not limited to such a determination method as mentioned above. For example, the values may be determined by using a system for actually measuring SAR. For example, the relationship of actually measured $B_1$ values and SAR is obtained beforehand, and the values of SAR and the upper limit of SAR may be obtained on the basis of that relationship.

Further, in the aforementioned method, the RF output is adjusted on the basis of the upper limit of SAR, but the RF output may be adjusted on the basis of the value of the output bound of RF amplifier. In this case, the condition calculation part 332 calculates a ratio of a certain RF output value and the output bound value of an RF amplifier, and when the ratio exceeds 1, adjusts the RF output value by using an amplitude of RF obtained by dividing the amplitude of RF of optimal radio frequency magnetic field condition for the distribution measurement section with the obtained ratio so that the RF output value does not exceed the output bound value of the RF amplifier.

In addition, also in this embodiment, other methods may be used as the method for calculating $B_1$ distribution, like the first embodiment. Further, the optimal radio frequency magnetic field condition may be either one of amplitude and phase of RF. Further, the direction of the imaging section may be an oblique direction. In such a case, the same countermeasures as those mentioned for the first embodiment may be used. Further, the number of distribution measurement sections may be determined according to change of the sectional shape of the subject for the measurement axis direction, the size of FOV, and so forth. Further, as the measurement axis direction, a desired direction may be chosen according to the imaging conditions and the imaging object. Further, the measurement axis direction may consist of two directions. Further, also in this embodiment, the optimal radio frequency magnetic field conditions may be set in a unit of region, like the first embodiment.

Further, when the distribution measurement section consists of a plurality of sections in this embodiment, $B_1$ non-uniformity reduction of the whole imaging region may be taken into consideration, like the second embodiment. That is, at the time of the RF shimming processing, for example, the optimal radio frequency magnetic field conditions for the distribution measurement sections are adjusted by using $B_1$ average values, or $B_1$ average values of the crossing regions are used, as mentioned for the second embodiment. By using such a configuration, the effect of the second embodiment can also be obtained.

The explanations of the aforementioned embodiments were made by exemplifying a 3T MRI apparatus and an RF transmission coil having two channels, but the aforementioned embodiments can be applied to a case of using a static magnetic field of an intensity higher than 3T or an RF transmission coil having channels in a number larger than 2.

Further, in the explanations of the aforementioned embodiments, the RF shimming part 330 is constructed in the computer 109 provided in the MRI apparatus 100, but the present invention is not limited to such a configuration. For example, it may be constructed in a general information processor independent from the MRI apparatus 100 and able to transmit and receive data to and from the MRI apparatus 100.

DENOTATION OF REFERENCE NUMERALS

100: MRI apparatus, 101: magnet, 102: gradient coil, 103: subject, 104: sequencer, 105: gradient magnetic field power supply, 106: radio frequency magnetic field generator, 107: table, 108: receiver, 109: computer, 110: display, 111: storage device, 112: shim coil, 113: shim power supply, 114: transmission coil, 115: reception coil, 201: feeding point, 202: phantom, 310: imaging position setting part, 320: static magnetic field shimming part, 330: RF shimming part, 331: distribution calculation part, 332: condition calculation part, 333: condition setting part, 334: distribution extraction part, 335: average calculation part, 336: output calculation part, 340: image acquisition part, 401: imaging section, 402: human pelvis region, 411: AX section, 412: SAG section, 413: COR section, 420: imaging region, 421: distribution measurement section, 422: distribution measurement section, 423: distribution measurement section, 510: imaging section, 511: distribution measurement section, 512: distribution measurement section, 513: distribution measurement section, 520: imaging section, 521: crossing region, 522: crossing region, 523: crossing region, 530: imaging section, 531: crossing region, 532: crossing region, 533: crossing region, 540: imaging section, 541: crossing region, 542: crossing region, 543: crossing region, 610: AX image, 611: AX section position, 621: SAG section position, 622: crossing region, 630: COR image, 632: crossing region, 641: uniformity index, 642: uniformity index, 643: uniformity index, 644: uniformity index, 651: uniformity index, 652: uniformity index, 653: uniformity index, 654: uniformity index, 661: uniformity index, 662: uniformity index, 663: uniformity index, 664: uniformity index, 711: AX section position, 721: SAG section position, 730: COR image, 741: uniformity index, 742: uniformity index, 743: uniformity index, 744: uniformity index, 751: uniformity index, 752: uniformity index, 753: uniformity index, 754: uniformity index, 761: uniformity index, 762: uniformity index, 763: uniformity index, 764: uniformity index, 810: AX image, 821: left side region, 822: center region, 823: right side region, 831: upper region, 832: center region, 833: lower region

The invention claimed is:

1. A magnetic resonance imaging apparatus comprising:
a static magnetic field formation part for forming a static magnetic field,
a gradient magnetic field application part for applying a gradient magnetic field,
a radio frequency magnetic field transmission part having a plurality of channels for transmitting different radio frequency magnetic fields to a subject,
a signal reception part for receiving magnetic resonance signals generated from the subject,
a distribution calculation part for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and a condition calculation part for calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution, wherein:

the imaging section is a section perpendicular to a second axis different from the first axis, the condition calculation part comprises:

a distribution extraction part for extracting a crossing region radio frequency magnetic field distribution as a radio frequency magnetic field distribution of a region containing a line of intersection of the imaging section and the first distribution measurement section from the first radio frequency magnetic field distribution, and the condition calculation part calculates the radio frequency magnetic field condition of the imaging section by using the crossing region radio frequency magnetic field distribution.

2. The magnetic resonance imaging apparatus according to claim 1, wherein:

the direction of the first axis is a direction along which a change of magnetic field distribution in an imaging space is smallest.

3. The magnetic resonance imaging apparatus according to claim 1, wherein:

the direction of the first axis is a direction along which a change of shape of the subject is smallest.

4. The magnetic resonance imaging apparatus according to claim 1, wherein:

the direction of the first axis is the axial direction.

5. The magnetic resonance imaging apparatus according to claim 1, wherein:

the second axis is perpendicular to the first axis.

6. The magnetic resonance imaging apparatus according to claim 5, wherein:

the direction of the first axis is a direction of an axis that passes through the body, and the direction of the second axis is the coronal direction or the sagittal direction.

7. The magnetic resonance imaging apparatus according to claim 1, wherein:

the region containing a line of intersection is a region larger than slice thickness of the imaging section.

8. The magnetic resonance imaging apparatus according to claim 7, wherein:

the region containing a line of intersection is a region of a strip shape having a width of 10 to 80 mm around the line of intersection.

9. The magnetic resonance imaging apparatus according to claim 1, wherein:

the condition calculation part comprises:

an output calculation part for calculating a ratio of SAR observed at the time of transmitting the radio frequency magnetic field from the radio frequency magnetic field transmission part under the calculated radio frequency magnetic field condition to a predetermined upper limit of SAR by using either one of the first radio frequency magnetic field distribution and the calculated radio frequency magnetic field condition, and when the result of the calculation performed by the output calculation performed by the output calculation part exceeds 1, the condition calculation part adjusts the radio frequency magnetic field condition so that the calculation result become 1 or smaller.

10. The magnetic resonance imaging apparatus according to claim 1, wherein:

the distribution calculation part further calculates a third radio frequency magnetic field distribution as a radio frequency magnetic field distribution of a third distribution measurement section perpendicular to a third axis different from the first axis, and the condition calculation part calculates the radio frequency magnetic field condition further on the basis of the third radio frequency magnetic field distribution.

11. A magnetic resonance imaging apparatus comprising:

a static magnetic field formation part for forming a static magnetic field, a gradient magnetic field application part for applying a gradient magnetic field, a radio frequency magnetic field transmission part having a plurality of channels for transmitting different radio frequency magnetic fields to a subject, a signal reception part for receiving magnetic resonance signals generated from the subject, a distribution calculation part for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and a condition calculation part for calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution, wherein:

the distribution calculation part further calculates a second radio frequency magnetic field distribution as a radio frequency magnetic field distribution of a second distribution measurement section perpendicular to the first axis from the magnetic resonance signals, and the condition calculation part calculates the radio frequency magnetic field condition further on the basis of the second radio frequency magnetic field distribution, and wherein:

the imaging section is a section perpendicular to the first axis and different from both the first distribution measurement section and the second distribution measurement section, and the condition calculation part calculates the radio frequency magnetic field condition for the imaging section by interpolation using a first radio frequency magnetic field condition calculated from the first radio frequency magnetic field distribution and a second radio frequency magnetic field condition calculated from the second radio frequency magnetic field distribution.

12. The magnetic resonance imaging apparatus according to claim 11, wherein:

the first distribution measurement section is a section at one end for the first axis direction of an imaging region including all the imaging sections, and the second distribution measurement section is a section of the other end for the first axis direction of the imaging region.

13. A magnetic resonance imaging apparatus comprising:

a static magnetic field formation part for forming a static magnetic field, a gradient magnetic field application part for applying a gradient magnetic field, a radio frequency magnetic field transmission part having a plurality of channels for transmitting different radio frequency magnetic fields to a subject,
a signal reception part for receiving magnetic resonance signals generated from the subject,
a distribution calculation part for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and
a condition calculation part for calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution, wherein:
the first distribution measurement section consists of a plurality of sections,
the imaging section is a section perpendicular to the first axis and different from any of the plurality of the first distribution measurement sections,
the condition calculation part further comprises an average calculation part for calculating a magnetic field average as an average value of radio frequency magnetic field values in each first distribution measurement section for each of the plurality of the first distribution measurement sections, and
the condition calculation part adjusts the radio frequency magnetic field conditions for the first measurement sections so that the magnetic field averages have the same values, and performs interpolation with the adjusted frequency magnetic field conditions to calculate the radio frequency magnetic field condition for the imaging section.

14. A magnetic resonance imaging apparatus comprising:
a static magnetic field formation part for forming a static magnetic field,
a gradient magnetic field application part for applying a gradient magnetic field,
a radio frequency magnetic field transmission part having a plurality of channels for transmitting different radio frequency magnetic fields to a subject,
a signal reception part for receiving magnetic resonance signals generated from the subject,
a distribution calculation part for calculating a first radio frequency magnetic field distribution as a radio frequency magnetic field distribution of a first distribution measurement section perpendicular to a first axis from the magnetic resonance signals received by the signal reception part after the radio frequency magnetic fields are transmitted from the radio frequency magnetic field transmission part to the subject, and
a condition calculation part for calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution, wherein:
the first distribution measurement section consists of a plurality of sections,
the imaging section is a section perpendicular to a second axis different from the first axis,
the condition calculation part comprises:
a distribution extraction part for extracting crossing region radio frequency magnetic field distributions as radio frequency magnetic field distributions of regions containing lines of intersection of the first distribution measurement sections and the imaging section from the first radio frequency magnetic field distributions, and
an average calculation part for calculating a magnetic field average as an average value of radio frequency magnetic field values in each of the regions containing the lines of intersection for every region, and
the condition calculation part calculates the radio frequency magnetic field condition for the imaging section so that the magnetic field averages have the same values.

15. A method for irradiating a radio frequency magnetic field in a magnetic resonance imaging apparatus comprising a radio frequency magnetic field transmission part having a plurality of channels for transmitting different radio frequency magnetic fields to a subject, and a signal reception part for receiving magnetic resonance signals generated from the subject, which comprises:
a distribution calculation step of calculating a first radio frequency magnetic field distribution as a radio frequency magnetic field distribution of a first distribution measurement section perpendicular to a first axis from the magnetic resonance signals detected by the signal reception part after the radio frequency magnetic fields are transmitted from the radio frequency magnetic field transmission part to the subject, and
a condition calculation step of calculating, as a radio frequency magnetic field condition, at least one of phase and amplitude of a radio frequency magnetic field irradiated from each of the plurality of the channels among imaging conditions for an arbitrary imaging section as an object of imaging on the basis of the first radio frequency magnetic field distribution, wherein the imaging section is a section perpendicular to a second axis different from the first axis, and wherein the condition calculation step further includes:
a distribution extraction step of extracting a crossing region radio frequency magnetic field distribution as a radio frequency magnetic field distribution of a region containing a line of intersection of the imaging section and the first distribution measurement section from the first radio frequency magnetic field distribution, and wherein the condition calculation step also includes a step of calculating the radio frequency magnetic field condition of the imaging section by using the crossing region radio frequency magnetic field distribution.

16. A program for making a computer function as:
a distribution calculation part for calculating a first radio frequency magnetic field distribution as a radio frequency magnetic field distribution of a first distribution measurement section perpendicular to a first axis from magnetic resonance signals received by a signal reception part of a magnetic resonance imaging apparatus, and
a condition calculation part for calculating, as a radio frequency magnetic field condition, at least one of phase and amplitude of a radio frequency magnetic field irradiated from each of a plurality of channels among imaging conditions for an arbitrary imaging section as an object of imaging on the basis of the first radio frequency magnetic field distribution, wherein:
the imaging section is a section perpendicular to a second axis different from the first axis, the condition calculation part comprises:
a distribution extraction part for extracting a crossing region radio frequency magnetic field distribution as a radio frequency magnetic field distribution of a region containing a line of intersection of the imaging section and the first distribution measurement section from the first radio frequency magnetic field distribution, and
the condition calculation part calculates the radio frequency magnetic field condition of the imaging section by using the crossing region radio frequency magnetic field distribution.

\* \* \* \* \*